(12) United States Patent
Jackson

(10) Patent No.: US 8,292,892 B2
(45) Date of Patent: *Oct. 23, 2012

(54) ORTHOPEDIC IMPLANT ROD REDUCTION TOOL SET AND METHOD

(76) Inventor: Roger P. Jackson, Prairie Village, KS (US)

( * ) Notice: Subject to any disclaimer, the term of this patent is extended or adjusted under 35 U.S.C. 154(b) by 138 days.

This patent is subject to a terminal disclaimer.

(21) Appl. No.: 12/454,152

(22) Filed: May 13, 2009

(65) Prior Publication Data

US 2009/0228056 A1    Sep. 10, 2009

(51) Int. Cl.
*A61F 5/00* (2006.01)
*A61B 17/58* (2006.01)

(52) U.S. Cl. .......................... 606/86 A; 606/96

(58) Field of Classification Search ............... 606/86 A, 606/86 R, 278, 99, 281, 256, 292, 279, 250, 606/264, 60, 79, 104; 81/452–458
See application file for complete search history.

(56) References Cited

U.S. PATENT DOCUMENTS

| | | |
|---|---|---|
| 854,956 A | 5/1907 | Martin |
| 1,472,464 A | 10/1923 | Ellison |
| 2,243,717 A | 5/1941 | Moreira |
| 2,346,346 A | 4/1944 | Anderson |
| 2,362,999 A | 11/1944 | Elmer |
| 2,524,095 A | 10/1950 | Williams |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 4,033,139 A | 7/1977 | Frederick |
| 4,041,939 A | 8/1977 | Hall |
| 4,190,091 A | 2/1980 | Colognori |
| 4,347,845 A | 9/1982 | Mayfield |

(Continued)

FOREIGN PATENT DOCUMENTS

CA    2577436    6/2006

(Continued)

OTHER PUBLICATIONS

Brochure of Spinal Concepts, *Pathfinder, Minimally Invasive Pedicle Fixation System*, Publication Date: May 2003.

(Continued)

*Primary Examiner* — Pedro Philogene
(74) *Attorney, Agent, or Firm* — John C. McMahon

(57) ABSTRACT

A tool set for implanting a rod in a human spine in conjunction with bone screws. The tool set includes a pair of end guide tools that receive opposite ends of the rod in channels and under manipulation by a surgeon facilitate transport of the rod toward the bone screws attached to the guide tools. Intermediate guide tools having guiding pass through slots are utilized to guide intermediate locations along the rod toward associated bone screws. An attachment structure operably connects the guide tools to the bone screws. The guide tools each include a lower guide and advancement structure to allow a closure top with mating structure to be rotated and driven downward against the rod and to cooperate with similar structure in the bone screw to seat and lock the rod therein. A method utilizing the tool set allows a surgeon to percutaneously implant the rod in the patient.

25 Claims, 13 Drawing Sheets

U.S. PATENT DOCUMENTS

| | | | |
|---|---|---|---|
| 4,373,754 A | 2/1983 | Bollfrass et al. | |
| 4,409,968 A | 10/1983 | Drummond | |
| 4,448,191 A | 5/1984 | Rodnyansky et al. | |
| 4,484,570 A | 11/1984 | Sutter et al. | |
| 4,600,224 A | 7/1986 | Blose | |
| 4,653,486 A | 3/1987 | Coker | |
| 4,703,954 A | 11/1987 | Ortloff et al. | |
| 4,707,001 A | 11/1987 | Johnson | |
| 4,743,260 A | 5/1988 | Burton | |
| 4,748,260 A | 5/1988 | Marlett | |
| 4,759,672 A | 7/1988 | Nilsen et al. | |
| 4,790,297 A | 12/1988 | Luque | |
| 4,836,196 A | 6/1989 | Park et al. | |
| 4,877,020 A | 10/1989 | Vich | |
| 4,887,596 A | 12/1989 | Sherman | |
| 4,946,458 A | 8/1990 | Harms et al. | |
| 4,950,269 A | 8/1990 | Gaines, Jr. | |
| 5,005,562 A | 4/1991 | Cotrel | |
| 5,015,247 A * | 5/1991 | Michelson | 606/247 |
| 5,019,080 A | 5/1991 | Hemer | |
| 5,020,519 A | 6/1991 | Hayes et al. | |
| 5,022,791 A | 6/1991 | Isler | |
| 5,034,011 A | 7/1991 | Howland | |
| 5,067,955 A | 11/1991 | Cotrel | |
| 5,084,048 A | 1/1992 | Jacob et al. | |
| 5,092,635 A | 3/1992 | DeLange et al. | |
| 5,092,866 A | 3/1992 | Breard et al. | |
| 5,102,412 A | 4/1992 | Rogozinski | |
| 5,129,388 A | 7/1992 | Vignaud et al. | |
| 5,147,363 A | 9/1992 | Harle | |
| 5,154,719 A | 10/1992 | Cotrel | |
| 5,176,483 A | 1/1993 | Baumann et al. | |
| 5,176,678 A | 1/1993 | Tsou | |
| 5,176,680 A | 1/1993 | Vignaud et al. | |
| 5,180,393 A | 1/1993 | Commarmond | |
| 5,207,678 A | 5/1993 | Harms et al. | |
| 5,217,497 A | 6/1993 | Mehdian | |
| 5,257,993 A | 11/1993 | Asher et al. | |
| 5,261,907 A | 11/1993 | Vignaud et al. | |
| 5,261,912 A | 11/1993 | Frigg | |
| 5,275,601 A | 1/1994 | Gogolewski et al. | |
| 5,282,862 A | 2/1994 | Baker et al. | |
| 5,282,863 A | 2/1994 | Burton | |
| D346,217 S | 4/1994 | Sparker et al. | |
| 5,306,275 A | 4/1994 | Bryan | |
| 5,312,404 A | 5/1994 | Asher et al. | |
| 5,321,901 A | 6/1994 | Kelly | |
| 5,330,472 A | 7/1994 | Metz-Stavenhagen | |
| 5,346,493 A | 9/1994 | Stahurski et al. | |
| 5,354,292 A * | 10/1994 | Braeuer et al. | 606/1 |
| 5,358,289 A | 10/1994 | Banker et al. | |
| 5,360,431 A | 11/1994 | Pino et al. | |
| 5,375,823 A | 12/1994 | Navas | |
| 5,385,583 A | 1/1995 | Cotrel | |
| 5,395,371 A | 3/1995 | Miller et al. | |
| 5,409,489 A | 4/1995 | Sioufi | |
| 5,415,661 A | 5/1995 | Holmes | |
| 5,423,816 A | 6/1995 | Lin | |
| 5,427,418 A | 6/1995 | Watts | |
| 5,429,639 A | 7/1995 | Judet | |
| 5,443,467 A | 8/1995 | Biedermann et al. | |
| 5,466,237 A | 11/1995 | Byrd, III et al. | |
| 5,468,241 A | 11/1995 | Metz-Stavenhagen et al. | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,480,401 A | 1/1996 | Navas | |
| 5,484,437 A | 1/1996 | Michelson | |
| 5,484,440 A | 1/1996 | Allard | |
| 5,487,742 A | 1/1996 | Cotrel | |
| 5,489,307 A | 2/1996 | Kuslich et al. | |
| 5,490,750 A | 2/1996 | Gundy | |
| 5,496,321 A | 3/1996 | Puno et al. | |
| 5,499,892 A | 3/1996 | Reed | |
| 5,505,731 A | 4/1996 | Tornier | |
| 5,507,745 A | 4/1996 | Logroscino et al. | |
| 5,540,688 A | 7/1996 | Navas | |
| 5,545,165 A | 8/1996 | Biedermann et al. | |
| 5,549,607 A | 8/1996 | Olson et al. | |
| 5,554,157 A | 9/1996 | Errico et al. | |
| 5,562,660 A | 10/1996 | Grob | |
| 5,562,663 A | 10/1996 | Wisnewski et al. | |
| 5,569,247 A | 10/1996 | Morrison | |
| 5,569,251 A | 10/1996 | Baker et al. | |
| 5,584,834 A | 12/1996 | Errico et al. | |
| 5,586,984 A | 12/1996 | Errico et al. | |
| 5,591,166 A | 1/1997 | Bernhardt et al. | |
| 5,601,553 A | 2/1997 | Trebing et al. | |
| 5,607,304 A | 3/1997 | Bailey et al. | |
| 5,607,425 A | 3/1997 | Rogozinski | |
| 5,607,426 A | 3/1997 | Ralph et al. | |
| 5,607,428 A | 3/1997 | Lin | |
| 5,611,800 A | 3/1997 | Davis et al. | |
| 5,628,740 A | 5/1997 | Mullane | |
| 5,630,817 A | 5/1997 | Rokegem | |
| 5,641,256 A | 6/1997 | Gundy | |
| 5,643,260 A | 7/1997 | Doherty | |
| 5,643,261 A | 7/1997 | Schafer et al. | |
| 5,647,873 A | 7/1997 | Errico et al. | |
| 5,662,652 A | 9/1997 | Schafer et al. | |
| 5,662,653 A | 9/1997 | Songer et al. | |
| 5,669,909 A | 9/1997 | Zdeblick et al. | |
| 5,669,911 A | 9/1997 | Errico et al. | |
| 5,672,175 A | 9/1997 | Martin | |
| 5,672,176 A | 9/1997 | Biedermann et al. | |
| 5,676,703 A | 10/1997 | Gelbard | |
| 5,681,319 A | 10/1997 | Biedermann et al. | |
| 5,683,390 A | 11/1997 | Metz-Stavenhagen et al. | |
| 5,690,630 A | 11/1997 | Errico et al. | |
| 5,697,929 A | 12/1997 | Mellinger | |
| 5,711,709 A | 1/1998 | McCoy | |
| 5,713,898 A | 2/1998 | Stucker et al. | |
| 5,716,356 A | 2/1998 | Biedermann et al. | |
| 5,720,751 A | 2/1998 | Jackson | |
| 5,723,013 A | 3/1998 | Jeanson et al. | |
| 5,725,527 A | 3/1998 | Biedermann et al. | |
| 5,725,528 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,741,254 A | 4/1998 | Henry et al. | |
| 5,752,957 A | 5/1998 | Ralph et al. | |
| 5,782,830 A | 7/1998 | Farris | |
| 5,782,833 A | 7/1998 | Haider | |
| 5,792,044 A | 8/1998 | Foley et al. | |
| 5,797,911 A | 8/1998 | Sherman et al. | |
| 5,800,435 A | 9/1998 | Errico et al. | |
| 5,800,547 A | 9/1998 | Schafer et al. | |
| 5,810,816 A | 9/1998 | Roussouly et al. | |
| 5,817,094 A | 10/1998 | Errico et al. | |
| 5,863,293 A | 1/1999 | Richelsoph | |
| 5,873,878 A | 2/1999 | Harms et al. | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,902,231 A | 5/1999 | Foley et al. | |
| RE36,221 E | 6/1999 | Breard et al. | |
| 5,910,141 A | 6/1999 | Morrison et al. | |
| 5,938,663 A | 8/1999 | Petreto | |
| 5,944,465 A | 8/1999 | Janitzki | |
| 5,951,553 A | 9/1999 | Betz | |
| 5,954,725 A | 9/1999 | Sherman et al. | |
| 5,961,517 A | 10/1999 | Biedermann et al. | |
| 5,964,760 A | 10/1999 | Richelsoph | |
| 6,001,098 A | 12/1999 | Metz-Stavenhagen et al. | |
| 6,004,349 A | 12/1999 | Jackson | |
| 6,010,503 A | 1/2000 | Richelsoph et al. | |
| 6,019,759 A | 2/2000 | Rogozinski | |
| 6,022,350 A | 2/2000 | Ganem | |
| 6,053,917 A | 4/2000 | Sherman et al. | |
| 6,059,786 A | 5/2000 | Jackson | |
| 6,063,088 A | 5/2000 | Winslow | |
| 6,063,090 A | 5/2000 | Schlapfer | |
| 6,074,391 A | 6/2000 | Metz-Stavenhagen et al. | |

| | | | |
|---|---|---|---|
| 6,077,262 A | 6/2000 | Schlapfer et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Saurat | |
| 6,102,912 A | 8/2000 | Cazin et al. | |
| 6,102,913 A | 8/2000 | Jackson | |
| 6,110,172 A | 8/2000 | Jackson | |
| 6,113,601 A | 9/2000 | Tatar | |
| 6,117,137 A | 9/2000 | Halm et al. | |
| 6,132,431 A | 10/2000 | Nilsson et al. | |
| 6,132,432 A | 10/2000 | Richelsoph | |
| 6,132,434 A | 10/2000 | Sherman et al. | |
| 6,136,002 A | 10/2000 | Shih et al. | |
| 6,139,549 A * | 10/2000 | Keller | 606/86 A |
| 6,143,032 A | 11/2000 | Schafer et al. | |
| 6,146,383 A | 11/2000 | Studer et al. | |
| 6,183,472 B1 | 2/2001 | Lutz | |
| 6,186,718 B1 | 2/2001 | Fogard | |
| 6,187,005 B1 | 2/2001 | Brace et al. | |
| 6,189,422 B1 | 2/2001 | Stihl | |
| 6,193,720 B1 | 2/2001 | Yuan et al. | |
| 6,214,012 B1 | 4/2001 | Karpman et al. | |
| RE37,161 E | 5/2001 | Michelson et al. | |
| 6,224,596 B1 | 5/2001 | Jackson | |
| 6,224,598 B1 | 5/2001 | Jackson | |
| 6,235,028 B1 | 5/2001 | Brumfield et al. | |
| 6,235,034 B1 | 5/2001 | Bray | |
| 6,241,730 B1 | 6/2001 | Alby | |
| 6,248,105 B1 | 6/2001 | Schlapfer et al. | |
| 6,248,107 B1 | 6/2001 | Foley et al. | |
| 6,251,112 B1 | 6/2001 | Jackson | |
| 6,254,146 B1 | 7/2001 | Church | |
| 6,254,602 B1 | 7/2001 | Justis | |
| 6,267,764 B1 | 7/2001 | Elberg | |
| 6,267,765 B1 | 7/2001 | Taylor et al. | |
| 6,273,888 B1 | 8/2001 | Justis | |
| 6,277,122 B1 | 8/2001 | McGahan et al. | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,290,700 B1 | 9/2001 | Schmotzer | |
| 6,296,642 B1 | 10/2001 | Morrison et al. | |
| 6,296,643 B1 | 10/2001 | Hopf et al. | |
| 6,299,613 B1 | 10/2001 | Ogilvie et al. | |
| 6,299,616 B1 | 10/2001 | Berger | |
| 6,302,888 B1 | 10/2001 | Mellinger et al. | |
| 6,309,391 B1 | 10/2001 | Crandall et al. | |
| 6,315,564 B1 | 11/2001 | Levisman | |
| 6,315,779 B1 | 11/2001 | Morrison et al. | |
| 6,331,179 B1 | 12/2001 | Freid et al. | |
| 6,355,040 B1 | 3/2002 | Richelsoph et al. | |
| RE37,665 E | 4/2002 | Ralph et al. | |
| 6,368,321 B1 | 4/2002 | Jackson | |
| 6,371,957 B1 | 4/2002 | Amrein et al. | |
| 6,402,752 B2 | 6/2002 | Schaffler-Wachter et al. | |
| 6,402,757 B1 | 6/2002 | Moore et al. | |
| 6,440,133 B1 | 8/2002 | Beale et al. | |
| 6,443,956 B1 | 9/2002 | Ray | |
| 6,451,021 B1 | 9/2002 | Ralph et al. | |
| 6,471,703 B1 | 10/2002 | Ashman | |
| 6,471,705 B1 | 10/2002 | Biedermann et al. | |
| 6,478,801 B1 | 11/2002 | Ralph et al. | |
| 6,485,491 B1 | 11/2002 | Farris et al. | |
| 6,485,492 B1 | 11/2002 | Halm et al. | |
| 6,485,494 B1 | 11/2002 | Haider | |
| 6,488,681 B2 | 12/2002 | Martin et al. | |
| 6,508,818 B2 | 1/2003 | Steiner et al. | |
| 6,511,484 B2 | 1/2003 | Torode et al. | |
| 6,520,962 B1 | 2/2003 | Taylor et al. | |
| 6,527,804 B1 | 3/2003 | Gauchet et al. | |
| 6,530,929 B1 | 3/2003 | Justis et al. | |
| 6,533,786 B1 | 3/2003 | Needham et al. | |
| 6,539,826 B2 | 4/2003 | Oesterle et al. | |
| 6,540,749 B2 | 4/2003 | Schafer et al. | |
| 6,547,790 B2 | 4/2003 | Harkey, III et al. | |
| 6,551,320 B2 | 4/2003 | Lieberman | |
| 6,551,323 B2 | 4/2003 | Doubler et al. | |
| 6,554,831 B1 | 4/2003 | Rivard et al. | |
| 6,554,832 B1 | 4/2003 | Shluzas | |
| 6,554,834 B1 | 4/2003 | Crozet et al. | |
| 6,558,387 B2 | 5/2003 | Errico et al. | |
| 6,562,038 B1 | 5/2003 | Morrison | |
| 6,562,040 B1 | 5/2003 | Wagner | |
| 6,565,565 B1 | 5/2003 | Yuan et al. | |
| 6,565,567 B1 | 5/2003 | Haider | |
| 6,572,618 B1 | 6/2003 | Morrison | |
| 6,582,436 B2 | 6/2003 | Schlapfer et al. | |
| 6,582,466 B2 | 6/2003 | Gauchet | |
| 6,585,740 B2 | 7/2003 | Schlapfer et al. | |
| 6,595,992 B1 | 7/2003 | Wagner et al. | |
| 6,595,993 B2 | 7/2003 | Donno et al. | |
| 6,599,294 B2 | 7/2003 | Fuss et al. | |
| 6,610,063 B2 | 8/2003 | Kumar et al. | |
| 6,613,050 B1 | 9/2003 | Wagner et al. | |
| 6,616,667 B1 | 9/2003 | Steiger et al. | |
| 6,616,669 B2 | 9/2003 | Ogilvie | |
| 6,623,485 B2 | 9/2003 | Doubler et al. | |
| 6,626,347 B2 | 9/2003 | Ng | |
| 6,626,907 B2 | 9/2003 | Campbell et al. | |
| 6,626,908 B2 | 9/2003 | Cooper et al. | |
| 6,635,059 B2 | 10/2003 | Randall et al. | |
| 6,635,060 B2 | 10/2003 | Hanson et al. | |
| 6,648,885 B1 | 11/2003 | Friesem | |
| 6,648,887 B2 | 11/2003 | Ashman | |
| 6,648,888 B1 | 11/2003 | Shluzas | |
| 6,652,526 B1 | 11/2003 | Arafiles | |
| 6,652,765 B1 | 11/2003 | Beaty | |
| 6,656,179 B1 | 12/2003 | Schaefer et al. | |
| 6,656,181 B2 | 12/2003 | Dixon et al. | |
| 6,660,004 B2 | 12/2003 | Barker et al. | |
| 6,660,006 B2 | 12/2003 | Markworth et al. | |
| 6,663,632 B1 | 12/2003 | Frigg | |
| 6,663,635 B2 | 12/2003 | Frigg et al. | |
| 6,673,073 B1 | 1/2004 | Schafer | |
| 6,676,661 B1 | 1/2004 | Benlloch et al. | |
| 6,679,833 B2 | 1/2004 | Smith et al. | |
| 6,682,529 B2 | 1/2004 | Stahurski | |
| 6,682,530 B2 | 1/2004 | Dixon et al. | |
| 6,689,133 B2 | 2/2004 | Morrison et al. | |
| 6,689,134 B2 | 2/2004 | Ralph et al. | |
| 6,695,843 B2 | 2/2004 | Biedermann et al. | |
| 6,695,851 B2 | 2/2004 | Zdeblick et al. | |
| 6,699,249 B2 | 3/2004 | Schlapfer et al. | |
| 6,706,045 B2 | 3/2004 | Lin et al. | |
| 6,712,818 B1 | 3/2004 | Michelson | |
| 6,716,213 B2 | 4/2004 | Shitoto | |
| 6,716,214 B1 | 4/2004 | Jackson | |
| 6,716,247 B2 | 4/2004 | Michelson | |
| 6,723,100 B2 | 4/2004 | Biedermann et al. | |
| 6,730,093 B2 | 5/2004 | Saint Martin | |
| 6,730,127 B2 | 5/2004 | Michelson | |
| 6,733,502 B2 | 5/2004 | Altarac et al. | |
| 6,736,816 B2 | 5/2004 | Ritland | |
| 6,736,820 B2 | 5/2004 | Bieeermann et al. | |
| 6,740,086 B2 | 5/2004 | Richelsoph | |
| 6,740,089 B2 | 5/2004 | Haider | |
| 6,743,231 B1 * | 6/2004 | Gray et al. | 606/86 A |
| 6,746,449 B2 | 6/2004 | Jones et al. | |
| 6,746,454 B2 | 6/2004 | Winterbottom et al. | |
| 6,755,829 B1 | 6/2004 | Bono et al. | |
| 6,755,835 B2 | 6/2004 | Schultheiss et al. | |
| 6,755,836 B1 | 6/2004 | Lewis | |
| 6,761,723 B2 | 7/2004 | Buttermann et al. | |
| 6,767,351 B2 | 7/2004 | Orbay et al. | |
| 6,770,075 B2 | 8/2004 | Howland | |
| 6,778,861 B1 | 8/2004 | Liebrecht et al. | |
| 6,780,186 B2 | 8/2004 | Errico et al. | |
| 6,783,527 B2 | 8/2004 | Drewry et al. | |
| 6,790,208 B2 | 9/2004 | Oribe et al. | |
| 6,790,209 B2 | 9/2004 | Beale et al. | |
| 6,802,844 B2 | 10/2004 | Ferree | |
| 6,827,719 B2 | 12/2004 | Ralph et al. | |
| 6,830,571 B2 | 12/2004 | Lenke et al. | |
| 6,835,196 B2 | 12/2004 | Biedermann et al. | |
| 6,837,889 B2 | 1/2005 | Shluzas | |
| 6,840,940 B2 | 1/2005 | Ralph et al. | |

| Patent No. | Date | Inventor(s) |
|---|---|---|
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,160,300 B2 * | 1/2007 | Jackson ............ 606/273 |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,250,052 B2 * | 7/2007 | Landry et al. ............ 606/86 A |
| 7,264,621 B2 | 9/2007 | Coates et al. |
| 7,270,665 B2 | 9/2007 | Morrison et al. |
| 7,282,064 B2 | 10/2007 | Chin |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,465,306 B2 * | 12/2008 | Pond et al. ............ 606/86 A |
| 7,476,238 B2 | 1/2009 | Panjabi |
| 7,491,208 B2 | 2/2009 | Pond, Jr. et al. |
| 7,491,218 B2 * | 2/2009 | Landry et al. ............ 606/246 |
| 7,556,639 B2 | 7/2009 | Rothman et al. |
| 7,559,942 B2 | 7/2009 | Paul et al. |
| 7,563,274 B2 | 7/2009 | Justis et al. |
| 7,563,283 B2 | 7/2009 | Kwak |
| 7,588,589 B2 | 9/2009 | Falahee |
| 7,601,166 B2 | 10/2009 | Biedermann et al. |
| 7,604,653 B2 | 10/2009 | Kitchen |
| 7,604,654 B2 | 10/2009 | Fallin et al. |
| 7,611,518 B2 | 11/2009 | Walder et al. |
| 7,615,068 B2 | 11/2009 | Timm et al. |
| 7,621,912 B2 | 11/2009 | Harms et al. |
| 7,621,940 B2 | 11/2009 | Harms et al. |
| 7,625,393 B2 | 12/2009 | Fallin et al. |
| 7,632,292 B2 | 12/2009 | Sengupta et al. |
| 7,641,673 B2 | 1/2010 | LeCouedic et al. |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,666,188 B2 * | 2/2010 | Anderson et al. ............ 606/104 |
| 7,682,375 B2 | 3/2010 | Ritland |
| 7,695,496 B2 | 4/2010 | Labrom et al. |
| 7,695,498 B2 | 4/2010 | Ritland |
| 7,695,514 B2 | 4/2010 | Kwak |
| 7,824,413 B2 * | 11/2010 | Varieur et al. ............ 606/99 |
| 2001/0001119 A1 | 5/2001 | Lombardo |
| 2001/0010000 A1 | 7/2001 | Gertzbein |
| 2001/0023350 A1 | 9/2001 | Choi |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0095153 A1 | 7/2002 | Jones et al. |
| 2002/0111626 A1 | 8/2002 | Ralph et al. |
| 2002/0133159 A1 | 9/2002 | Jackson |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208203 A1 | 11/2003 | Lim et al. |
| 2003/0208204 A1 | 11/2003 | Bailey et al. |
| 2003/0212398 A1 | 11/2003 | Jackson |

| | | | | | | |
|---|---|---|---|---|---|---|
| 2003/0216735 A1 | 11/2003 | Altarac et al. | | 2005/0187555 A1 | 8/2005 | Biedermann et al. |
| 2003/0220642 A1 | 11/2003 | Fruediger | | 2005/0192571 A1 | 9/2005 | Abdelgany |
| 2003/0220643 A1 | 11/2003 | Ferree | | 2005/0192580 A1 | 9/2005 | Dalton |
| 2003/0225408 A1 | 12/2003 | Nichols et al. | | 2005/0192589 A1 | 9/2005 | Raymond |
| 2003/0236529 A1 | 12/2003 | Shluzas et al. | | 2005/0203511 A1 | 9/2005 | Wilson-MacDonald et al. |
| 2004/0002708 A1 | 1/2004 | Ritland | | 2005/0203513 A1 | 9/2005 | Jahng et al. |
| 2004/0006342 A1 | 1/2004 | Altarac et al. | | 2005/0203514 A1 | 9/2005 | Jahng et al. |
| 2004/0039384 A1 | 2/2004 | Boehm | | 2005/0203516 A1 | 9/2005 | Biedermann et al. |
| 2004/0049189 A1 | 3/2004 | Le Couudic et al. | | 2005/0203517 A1 | 9/2005 | Jahng et al. |
| 2004/0049190 A1 | 3/2004 | Biedermann et al. | | 2005/0203518 A1 | 9/2005 | Biedermann et al. |
| 2004/0073215 A1 | 4/2004 | Carli | | 2005/0203519 A1 | 9/2005 | Harms et al. |
| 2004/0078082 A1 | 4/2004 | Lange | | 2005/0216001 A1 | 9/2005 | David |
| 2004/0087949 A1 | 5/2004 | Bono et al. | | 2005/0216003 A1 | 9/2005 | Biedermann et al. |
| 2004/0087952 A1 | 5/2004 | Borgstrom et al. | | 2005/0228400 A1 | 10/2005 | Chao |
| 2004/0092934 A1 | 5/2004 | Howland | | 2005/0228501 A1 | 10/2005 | Miller et al. |
| 2004/0097933 A1 | 5/2004 | Lourdel et al. | | 2005/0234450 A1 | 10/2005 | Barker |
| 2004/0116929 A1 | 6/2004 | Barker et al. | | 2005/0234451 A1 | 10/2005 | Markworth |
| 2004/0133207 A1 | 7/2004 | Abdou | | 2005/0234452 A1 | 10/2005 | Malandain |
| 2004/0138662 A1 | 7/2004 | Landry et al. | | 2005/0234453 A1 | 10/2005 | Shaolian et al. |
| 2004/0143265 A1 | 7/2004 | Landry et al. | | 2005/0234454 A1 | 10/2005 | Chin |
| 2004/0147928 A1 | 7/2004 | Landry et al. | | 2005/0234456 A1 | 10/2005 | Malandain |
| 2004/0147929 A1 | 7/2004 | Biedermann et al. | | 2005/0240181 A1 | 10/2005 | Boomer et al. |
| 2004/0158247 A1 | 8/2004 | Sitiso et al. | | 2005/0240183 A1 | 10/2005 | Vaughan |
| 2004/0162560 A1 | 8/2004 | Raynor et al. | | 2005/0245930 A1 | 11/2005 | Timm et al. |
| 2004/0172022 A1 | 9/2004 | Landry et al. | | 2005/0251137 A1 | 11/2005 | Ball |
| 2004/0172025 A1 | 9/2004 | Drewry et al. | | 2005/0251139 A1 | 11/2005 | Roh |
| 2004/0176766 A1 | 9/2004 | Shluzas | | 2005/0251140 A1 | 11/2005 | Shaolian et al. |
| 2004/0186473 A1 | 9/2004 | Cournoyer et al. | | 2005/0251141 A1 | 11/2005 | Frigg et al. |
| 2004/0210216 A1 | 10/2004 | Farris et al. | | 2005/0260058 A1 | 11/2005 | Cassagne, III |
| 2004/0220567 A1 | 11/2004 | Eisermann | | 2005/0261685 A1 | 11/2005 | Fortin et al. |
| 2004/0220671 A1 | 11/2004 | Ralph et al. | | 2005/0261687 A1 | 11/2005 | Garamszegi et al. |
| 2004/0225289 A1 | 11/2004 | Biedermann et al. | | 2005/0267470 A1 | 12/2005 | McBride |
| 2004/0236327 A1 | 11/2004 | Paul et al. | | 2005/0267471 A1 | 12/2005 | Biedermann et al. |
| 2004/0236328 A1 | 11/2004 | Paul et al. | | 2005/0267474 A1 | 12/2005 | Dalton |
| 2004/0236329 A1 | 11/2004 | Panjabi | | 2005/0267477 A1 | 12/2005 | Jackson |
| 2004/0236330 A1 | 11/2004 | Purcell et al. | | 2005/0273099 A1 | 12/2005 | Baccelli et al. |
| 2004/0249380 A1 | 12/2004 | Glascott | | 2005/0273101 A1 | 12/2005 | Schumacher |
| 2004/0267264 A1 | 12/2004 | Konieczynski et al. | | 2005/0277919 A1 | 12/2005 | Slivka et al. |
| 2005/0027296 A1 | 2/2005 | Thramann et al. | | 2005/0277922 A1 | 12/2005 | Trieu et al. |
| 2005/0033298 A1 | 2/2005 | Hawkes et al. | | 2005/0277923 A1 | 12/2005 | Sweeney |
| 2005/0038432 A1 | 2/2005 | Shaolian et al. | | 2005/0277925 A1 | 12/2005 | Mujwid |
| 2005/0049708 A1 | 3/2005 | Atkinson et al. | | 2005/0277927 A1 | 12/2005 | Guenther et al. |
| 2005/0055026 A1 | 3/2005 | Biedermann et al. | | 2005/0277928 A1 | 12/2005 | Boschert |
| 2005/0065514 A1 | 3/2005 | Studer | | 2005/0277931 A1 | 12/2005 | Sweeney et al. |
| 2005/0065515 A1 | 3/2005 | Jahng | | 2005/0277934 A1 | 12/2005 | Vardiman |
| 2005/0065516 A1 | 3/2005 | Jahng | | 2005/0283152 A1 | 12/2005 | Lindemann et al. |
| 2005/0065517 A1 | 3/2005 | Chin | | 2005/0283157 A1 | 12/2005 | Coates et al. |
| 2005/0070899 A1 | 3/2005 | Doubler et al. | | 2005/0283238 A1 | 12/2005 | Reiley |
| 2005/0080415 A1 | 4/2005 | Keyer et al. | | 2005/0283244 A1 | 12/2005 | Gordon et al. |
| 2005/0085812 A1 | 4/2005 | Sherman | | 2005/0288669 A1 | 12/2005 | Abdou |
| 2005/0085813 A1 | 4/2005 | Spitler et al. | | 2005/0288670 A1 | 12/2005 | Panjabi et al. |
| 2005/0085815 A1 | 4/2005 | Harms et al. | | 2005/0288671 A1 | 12/2005 | Yuan et al. |
| 2005/0085816 A1 | 4/2005 | Michelson | | 2005/0288672 A1 | 12/2005 | Ferree |
| 2005/0096652 A1 | 5/2005 | Burton | | 2005/0288673 A1 | 12/2005 | Catbagan et al. |
| 2005/0096654 A1 | 5/2005 | Lin | | 2006/0004357 A1 | 1/2006 | Lee et al. |
| 2005/0107788 A1 | 5/2005 | Beaurain et al. | | 2006/0004359 A1 | 1/2006 | Kramer et al. |
| 2005/0113927 A1 | 5/2005 | Malek | | 2006/0004360 A1 | 1/2006 | Kramer et al. |
| 2005/0124991 A1 | 6/2005 | Jahng | | 2006/0004363 A1 | 1/2006 | Brockmeyer et al. |
| 2005/0131404 A1 | 6/2005 | Mazda et al. | | 2006/0009767 A1 | 1/2006 | Kiester |
| 2005/0131407 A1 | 6/2005 | Sicvol et al. | | 2006/0009768 A1 | 1/2006 | Ritland |
| 2005/0131413 A1 | 6/2005 | O'Driscoll et al. | | 2006/0009769 A1 | 1/2006 | Liebermann |
| 2005/0137597 A1 | 6/2005 | Butler et al. | | 2006/0009770 A1 | 1/2006 | Speirs et al. |
| 2005/0143737 A1 | 6/2005 | Pafford et al. | | 2006/0009775 A1 | 1/2006 | Dec et al. |
| 2005/0143823 A1 | 6/2005 | Boyd et al. | | 2006/0009780 A1 | 1/2006 | Foley et al. |
| 2005/0149020 A1 | 7/2005 | Jahng | | 2006/0009846 A1 | 1/2006 | Trieu et al. |
| 2005/0149023 A1 | 7/2005 | Ritland | | 2006/0015099 A1 | 1/2006 | Cannon et al. |
| 2005/0149053 A1 | 7/2005 | Varieur | | 2006/0015104 A1 | 1/2006 | Dalton |
| 2005/0154389 A1 | 7/2005 | Selover et al. | | 2006/0025767 A1 | 2/2006 | Khalili |
| 2005/0154390 A1 | 7/2005 | Biedermann et al. | | 2006/0025768 A1 | 2/2006 | Iott et al. |
| 2005/0154391 A1 | 7/2005 | Doherty et al. | | 2006/0025770 A1 | 2/2006 | Schlapfer et al. |
| 2005/0159750 A1 | 7/2005 | Doherty | | 2006/0030850 A1 | 2/2006 | Keegan et al. |
| 2005/0165400 A1 | 7/2005 | Fernandez | | 2006/0036240 A1 | 2/2006 | Colleran |
| 2005/0171540 A1 | 8/2005 | Lim et al. | | 2006/0036242 A1 | 2/2006 | Nilsson et al. |
| 2005/0171542 A1 | 8/2005 | Biedermann et al. | | 2006/0036244 A1 | 2/2006 | Spitler et al. |
| 2005/0171543 A1 | 8/2005 | Timm et al. | | 2006/0036246 A1 | 2/2006 | Carl et al. |
| 2005/0177157 A1 | 8/2005 | Jahng | | 2006/0036252 A1 | 2/2006 | Baynham et al. |
| 2005/0182401 A1 | 8/2005 | Timm et al. | | 2006/0036254 A1 | 2/2006 | Lim |
| 2005/0182410 A1 | 8/2005 | Jackson | | 2006/0036256 A1 | 2/2006 | Carl et al. |
| 2005/0187548 A1 | 8/2005 | Butler et al. | | 2006/0036259 A1 | 2/2006 | Carl et al. |

| | | | | | |
|---|---|---|---|---|---|
| 2006/0036260 A1 | 2/2006 | Runco et al. | 2006/0210494 A1 | 9/2006 | Rabiei et al. |
| 2006/0036323 A1 | 2/2006 | Carl et al. | 2006/0212033 A1 | 9/2006 | Rothman |
| 2006/0036324 A1 | 2/2006 | Sachs et al. | 2006/0212034 A1 | 9/2006 | Triplett et al. |
| 2006/0041259 A1 | 2/2006 | Paul et al. | 2006/0217713 A1 | 9/2006 | Serhan et al. |
| 2006/0052780 A1 | 3/2006 | Errico et al. | 2006/0217714 A1 | 9/2006 | Serhan et al. |
| 2006/0052783 A1 | 3/2006 | Dant et al. | 2006/0217715 A1 | 9/2006 | Albert et al. |
| 2006/0052784 A1 | 3/2006 | Dant et al. | 2006/0217716 A1 | 9/2006 | Baker et al. |
| 2006/0052786 A1 | 3/2006 | Dant et al. | 2006/0229608 A1 | 10/2006 | Foster |
| 2006/0058788 A1 | 3/2006 | Hammer et al. | 2006/0229609 A1 | 10/2006 | Wang |
| 2006/0058790 A1 | 3/2006 | Carl et al. | 2006/0229612 A1 | 10/2006 | Rothman |
| 2006/0064090 A1 | 3/2006 | Park | 2006/0229613 A1 | 10/2006 | Timm |
| 2006/0064091 A1 | 3/2006 | Ludwig et al. | 2006/0229614 A1 | 10/2006 | Foley et al. |
| 2006/0064092 A1 | 3/2006 | Howland | 2006/0229615 A1 | 10/2006 | Abdou |
| 2006/0069390 A1 | 3/2006 | Frigg | 2006/0235389 A1 | 10/2006 | Albert et al. |
| 2006/0074419 A1 | 4/2006 | Taylor et al. | 2006/0235392 A1 | 10/2006 | Hammer et al. |
| 2006/0079894 A1 | 4/2006 | Colleran et al. | 2006/0235393 A1 | 10/2006 | Bono et al. |
| 2006/0079895 A1 | 4/2006 | McLeer | 2006/0241593 A1 | 10/2006 | Sherman et al. |
| 2006/0079896 A1 | 4/2006 | Kwak | 2006/0241595 A1 | 10/2006 | Molz, IV. et al. |
| 2006/0079898 A1 | 4/2006 | Ainsworth | 2006/0241599 A1 | 10/2006 | Konieczynski et al. |
| 2006/0079899 A1 | 4/2006 | Ritland | 2006/0241600 A1 | 10/2006 | Ensign et al. |
| 2006/0084977 A1 | 4/2006 | Lieberman | 2006/0241769 A1 | 10/2006 | Gordon |
| 2006/0084981 A1 | 4/2006 | Shluzas | 2006/0241771 A1 | 10/2006 | Gordon |
| 2006/0084982 A1 | 4/2006 | Kim | 2006/0247624 A1 | 11/2006 | Banouskou et al. |
| 2006/0084983 A1 | 4/2006 | Kim | 2006/0247630 A1 | 11/2006 | Iott et al. |
| 2006/0084984 A1 | 4/2006 | Kim | 2006/0247631 A1 | 11/2006 | Ahn et al. |
| 2006/0084985 A1 | 4/2006 | Kim | 2006/0247632 A1 | 11/2006 | Winslow |
| 2006/0084987 A1 | 4/2006 | Kim | 2006/0247633 A1 | 11/2006 | Winslow |
| 2006/0084988 A1 | 4/2006 | Kim | 2006/0247635 A1 | 11/2006 | Gordon |
| 2006/0084989 A1 | 4/2006 | Dickinson et al. | 2006/0247636 A1 | 11/2006 | Yuan et al. |
| 2006/0084991 A1 | 4/2006 | Borgstrom | 2006/0247637 A1 | 11/2006 | Colleran |
| 2006/0084993 A1 | 4/2006 | Landry et al. | 2006/0247779 A1 | 11/2006 | Gordon |
| 2006/0084995 A1 | 4/2006 | Biedermann et al. | 2006/0264933 A1 | 11/2006 | Baker et al. |
| 2006/0085069 A1 | 4/2006 | Kim | 2006/0264934 A1 | 11/2006 | Fallin |
| 2006/0089643 A1 | 4/2006 | Mujwid | 2006/0264935 A1 | 11/2006 | White |
| 2006/0089644 A1 | 4/2006 | Felix | 2006/0264936 A1 | 11/2006 | Partin et al. |
| 2006/0095037 A1 | 5/2006 | Jones et al. | 2006/0264937 A1 | 11/2006 | White |
| 2006/0106380 A1 | 5/2006 | Colleran et al. | 2006/0264940 A1 | 11/2006 | Hartmannt |
| 2006/0106381 A1 | 5/2006 | Ferree | 2006/0264942 A1 | 11/2006 | Lim et al. |
| 2006/0106383 A1 | 5/2006 | Biedermann et al. | 2006/0264962 A1 | 11/2006 | Chin et al. |
| 2006/0111714 A1 | 5/2006 | Foley | 2006/0276787 A1 | 12/2006 | Zubok et al. |
| 2006/0111715 A1 | 5/2006 | Jackson | 2006/0276789 A1 | 12/2006 | Jackson |
| 2006/0116677 A1 | 6/2006 | Burd et al. | 2006/0276791 A1 | 12/2006 | Shluzas |
| 2006/0122597 A1 | 6/2006 | Jones et al. | 2006/0276792 A1 | 12/2006 | Ensign et al. |
| 2006/0122599 A1 | 6/2006 | Drewry | 2006/0282074 A1 | 12/2006 | Renaud et al. |
| 2006/0129147 A1 | 6/2006 | Biedermann et al. | 2006/0282075 A1 | 12/2006 | Labrom |
| 2006/0129149 A1 | 6/2006 | Iott et al. | 2006/0282076 A1 | 12/2006 | Labrom |
| 2006/0129239 A1 | 6/2006 | Kwak | 2006/0282077 A1 | 12/2006 | Labrom |
| 2006/0142758 A1 | 6/2006 | Petit | 2006/0282078 A1 | 12/2006 | Labrom |
| 2006/0142760 A1 | 6/2006 | McDonnell | 2006/0282079 A1 | 12/2006 | Labrom |
| 2006/0142761 A1 | 6/2006 | Landry et al. | 2006/0282080 A1 | 12/2006 | Albert |
| 2006/0149228 A1 | 7/2006 | Schlapfer | 2006/0293657 A1 | 12/2006 | Hartmann |
| 2006/0149229 A1 | 7/2006 | Kwak | 2006/0293659 A1 | 12/2006 | Alvarez |
| 2006/0149232 A1 | 7/2006 | Sasing | 2006/0293663 A1 | 12/2006 | Walkenhorst |
| 2006/0149238 A1 | 7/2006 | Sherman et al. | 2006/0293665 A1 | 12/2006 | Shluzas |
| 2006/0149241 A1 | 7/2006 | Richelsoph et al. | 2006/0293666 A1 | 12/2006 | Matthis et al. |
| 2006/0149244 A1 | 7/2006 | Amrein et al. | 2007/0005062 A1 | 1/2007 | Lange |
| 2006/0155277 A1 | 7/2006 | Metz-Stavenhagen | 2007/0005063 A1 | 1/2007 | Bruneau |
| 2006/0155278 A1 | 7/2006 | Warnick | 2007/0005137 A1 | 1/2007 | Kwak |
| 2006/0161152 A1 | 7/2006 | Ensign et al. | 2007/0016188 A1 | 1/2007 | Boehm, Jr. et al. |
| 2006/0167454 A1 | 7/2006 | Ludwig et al. | 2007/0016190 A1 | 1/2007 | Martinez |
| 2006/0167455 A1 | 7/2006 | Clement et al. | 2007/0016193 A1 | 1/2007 | Ritland |
| 2006/0173454 A1 | 8/2006 | Spitler et al. | 2007/0016194 A1 | 1/2007 | Shaolian et al. |
| 2006/0173456 A1 | 8/2006 | Hawkes et al. | 2007/0016198 A1 | 1/2007 | Boehm, Jr. et al. |
| 2006/0184171 A1 | 8/2006 | Biedermann | 2007/0016199 A1 | 1/2007 | Boehm, Jr. et al. |
| 2006/0184180 A1 | 8/2006 | Augostino | 2007/0021750 A1 | 1/2007 | Shluzas et al. |
| 2006/0189983 A1 | 8/2006 | Fallin | 2007/0043355 A1 | 2/2007 | Bette et al. |
| 2006/0189984 A1 | 8/2006 | Fallin | 2007/0043356 A1 | 2/2007 | Timm |
| 2006/0189985 A1 | 8/2006 | Lewis | 2007/0043357 A1 | 2/2007 | Kirschman |
| 2006/0195090 A1 | 8/2006 | Suddaby | 2007/0043358 A1 | 2/2007 | Molz, IV et al. |
| 2006/0195093 A1 | 8/2006 | Jahng | 2007/0043359 A1 | 2/2007 | Altarac et al. |
| 2006/0195098 A1 | 8/2006 | Schumacher | 2007/0043364 A1 | 2/2007 | Cawley et al. |
| 2006/0200128 A1 | 9/2006 | Mueller | 2007/0049931 A1 | 3/2007 | Justis et al. |
| 2006/0200130 A1 | 9/2006 | Hawkins | 2007/0049933 A1 | 3/2007 | Ahn et al. |
| 2006/0200131 A1 | 9/2006 | Chao et al. | 2007/0049936 A1 | 3/2007 | Colleran |
| 2006/0200132 A1 | 9/2006 | Chao et al. | 2007/0055235 A1 | 3/2007 | Janowski et al. |
| 2006/0200135 A1 | 9/2006 | Sherman et al. | 2007/0055236 A1 | 3/2007 | Hudgins |
| 2006/0200138 A1 | 9/2006 | Michelson | 2007/0055238 A1 | 3/2007 | Biedermann et al. |
| 2006/0200139 A1 | 9/2006 | Michelson | 2007/0055239 A1 | 3/2007 | Sweeney et al. |
| 2006/0200149 A1 | 9/2006 | Hoy et al. | 2007/0055240 A1 | 3/2007 | Matthis et al. |

| | | | | | | |
|---|---|---|---|---|---|---|
| 2007/0055241 A1 | 3/2007 | Matthis et al. | | 2007/0260246 A1 | 11/2007 | Biedermann |
| 2007/0055242 A1 | 3/2007 | Bailly | | 2007/0270806 A1 | 11/2007 | Foley et al. |
| 2007/0055244 A1 | 3/2007 | Jackson | | 2007/0270807 A1 | 11/2007 | Armstrong et al. |
| 2007/0055247 A1 | 3/2007 | Jahng | | 2007/0270810 A1 | 11/2007 | Sanders |
| 2007/0073289 A1 | 3/2007 | Kwak | | 2007/0270813 A1 | 11/2007 | Garamszegi |
| 2007/0073290 A1 | 3/2007 | Boehm, Jr. | | 2007/0270814 A1 | 11/2007 | Lim et al. |
| 2007/0073291 A1 | 3/2007 | Cordaro et al. | | 2007/0270815 A1 | 11/2007 | Johnson et al. |
| 2007/0073293 A1 | 3/2007 | Martz | | 2007/0270821 A1 | 11/2007 | Trieu et al. |
| 2007/0073294 A1 | 3/2007 | Chin et al. | | 2007/0270830 A1 | 11/2007 | Morrison |
| 2007/0078460 A1 | 4/2007 | Frigg et al. | | 2007/0270831 A1 | 11/2007 | Dewey et al. |
| 2007/0078461 A1 | 4/2007 | Shluzas | | 2007/0270832 A1 | 11/2007 | Moore |
| 2007/0083199 A1 | 4/2007 | Baccelli | | 2007/0270835 A1 | 11/2007 | Wisnewski |
| 2007/0088357 A1 | 4/2007 | Johnson et al. | | 2007/0270837 A1 | 11/2007 | Eckhardt et al. |
| 2007/0088359 A1 | 4/2007 | Woods et al. | | 2007/0270838 A1 | 11/2007 | Bruneau et al. |
| 2007/0093813 A1 | 4/2007 | Callahan, II et al. | | 2007/0270839 A1 | 11/2007 | Jeon et al. |
| 2007/0093814 A1 | 4/2007 | Callahan, II et al. | | 2007/0270843 A1 | 11/2007 | Matthis et al. |
| 2007/0093815 A1 | 4/2007 | Callahan, II et al. | | 2007/0276380 A1 | 11/2007 | Jahng et al. |
| 2007/0093817 A1 | 4/2007 | Barrus et al. | | 2007/0288004 A1 | 12/2007 | Alvarez |
| 2007/0093818 A1 | 4/2007 | Biedermann et al. | | 2007/0288008 A1 | 12/2007 | Park |
| 2007/0093819 A1 | 4/2007 | Albert | | 2007/0288009 A1 | 12/2007 | Brown et al. |
| 2007/0093824 A1 | 4/2007 | Hestad et al. | | 2007/0288011 A1 | 12/2007 | Logan |
| 2007/0093826 A1 | 4/2007 | Hawkes et al. | | 2007/0288012 A1 | 12/2007 | Colleran et al. |
| 2007/0093827 A1 | 4/2007 | Warnick | | 2008/0009862 A1 | 1/2008 | Hoffman |
| 2007/0093828 A1 | 4/2007 | Abdou | | 2008/0009864 A1 | 1/2008 | Forton et al. |
| 2007/0093831 A1 | 4/2007 | Abdelgany et al. | | 2008/0015578 A1 | 1/2008 | Erickson et al. |
| 2007/0093833 A1 | 4/2007 | Kuiper et al. | | 2008/0015579 A1 | 1/2008 | Whipple |
| 2007/0100341 A1 | 5/2007 | Reglos et al. | | 2008/0015580 A1 | 1/2008 | Chao |
| 2007/0118117 A1 | 5/2007 | Altarac et al. | | 2008/0015584 A1 | 1/2008 | Richelsoph |
| 2007/0118118 A1 | 5/2007 | Kwak et al. | | 2008/0015586 A1 | 1/2008 | Krishna et al. |
| 2007/0118119 A1 | 5/2007 | Hestad | | 2008/0021454 A1 | 1/2008 | Chao et al. |
| 2007/0118122 A1 | 5/2007 | Butler et al. | | 2008/0021455 A1 | 1/2008 | Chao et al. |
| 2007/0118123 A1 | 5/2007 | Strausbaugh et al. | | 2008/0021458 A1 | 1/2008 | Lim |
| 2007/0118124 A1 | 5/2007 | Biedermann et al. | | 2008/0021459 A1 | 1/2008 | Lim |
| 2007/0123862 A1 | 5/2007 | Warnick | | 2008/0021462 A1 | 1/2008 | Trieu |
| 2007/0123864 A1 | 5/2007 | Walder et al. | | 2008/0021464 A1 | 1/2008 | Norin et al. |
| 2007/0123865 A1 | 5/2007 | Schlapfer et al. | | 2008/0021465 A1 | 1/2008 | Shadduck et al. |
| 2007/0123866 A1 | 5/2007 | Gerbec et al. | | 2008/0021466 A1 | 1/2008 | Shadduck et al. |
| 2007/0123867 A1 | 5/2007 | Kirschman | | 2008/0021473 A1 | 1/2008 | Butler et al. |
| 2007/0123870 A1 | 5/2007 | Jeon et al. | | 2008/0027432 A1 | 1/2008 | Strauss et al. |
| 2007/0123871 A1 | 5/2007 | Jahng | | 2008/0033435 A1 | 2/2008 | Studer et al. |
| 2007/0129729 A1 | 6/2007 | Petit et al. | | 2008/0039838 A1 | 2/2008 | Landry et al. |
| 2007/0135815 A1 | 6/2007 | Gerbec et al. | | 2008/0039843 A1 | 2/2008 | Abdou |
| 2007/0161986 A1 | 7/2007 | Levy | | 2008/0045951 A1 | 2/2008 | Fanger et al. |
| 2007/0161991 A1 | 7/2007 | Altarac et al. | | 2008/0045955 A1 | 2/2008 | Berrevoets et al. |
| 2007/0161994 A1 | 7/2007 | Lowrey et al. | | 2008/0045957 A1 | 2/2008 | Landry et al. |
| 2007/0161995 A1 | 7/2007 | Trautwein et al. | | 2008/0051780 A1 | 2/2008 | Vaidya et al. |
| 2007/0161996 A1 | 7/2007 | Biedermann et al. | | 2008/0051787 A1 | 2/2008 | Remington et al. |
| 2007/0161997 A1 | 7/2007 | Thramann et al. | | 2008/0058811 A1 | 3/2008 | Alleyne et al. |
| 2007/0161999 A1 | 7/2007 | Biedermann et al. | | 2008/0058812 A1 | 3/2008 | Zehnder |
| 2007/0167948 A1 | 7/2007 | Abdou | | 2008/0065071 A1 | 3/2008 | Park |
| 2007/0167949 A1 | 7/2007 | Altarac et al. | | 2008/0065073 A1 | 3/2008 | Perriello et al. |
| 2007/0173818 A1 | 7/2007 | Hestad et al. | | 2008/0065075 A1 | 3/2008 | Dant |
| 2007/0173819 A1 | 7/2007 | Sandlin | | 2008/0065077 A1 | 3/2008 | Ferree |
| 2007/0173820 A1 | 7/2007 | Trieu | | 2008/0065079 A1 | 3/2008 | Bruneau et al. |
| 2007/0173822 A1 | 7/2007 | Bruneau et al. | | 2008/0071273 A1 | 3/2008 | Hawkes et al. |
| 2007/0173828 A1 | 7/2007 | Firkins et al. | | 2008/0071274 A1 | 3/2008 | Ensign |
| 2007/0173832 A1 | 7/2007 | Tebbe et al. | | 2008/0071277 A1 | 3/2008 | Warnick |
| 2007/0191839 A1 | 8/2007 | Justis et al. | | 2008/0077139 A1 | 3/2008 | Landry et al. |
| 2007/0191841 A1 | 8/2007 | Justis et al. | | 2008/0086131 A1 | 4/2008 | Daly et al. |
| 2007/0191846 A1 | 8/2007 | Bruneau et al. | | 2008/0086132 A1 | 4/2008 | Biedermann et al. |
| 2007/0198014 A1 | 8/2007 | Graf et al. | | 2008/0091214 A1 | 4/2008 | Richelsoph |
| 2007/0208344 A1 | 9/2007 | Young | | 2008/0097431 A1 | 4/2008 | Vessa |
| 2007/0213720 A1 | 9/2007 | Gordon et al. | | 2008/0097434 A1 | 4/2008 | Moumene et al. |
| 2007/0225707 A1 | 9/2007 | Wisnewski et al. | | 2008/0097441 A1 | 4/2008 | Hayes et al. |
| 2007/0225708 A1 | 9/2007 | Biedermann et al. | | 2008/0097457 A1 | 4/2008 | Warnick |
| 2007/0225710 A1 | 9/2007 | Jahng et al. | | 2008/0108992 A1 | 5/2008 | Barry et al. |
| 2007/0225711 A1 | 9/2007 | Ensign | | 2008/0119858 A1 | 5/2008 | Potash |
| 2007/0233064 A1 | 10/2007 | Holt | | 2008/0125777 A1 | 5/2008 | Veldman et al. |
| 2007/0233073 A1 | 10/2007 | Wisnewski et al. | | 2008/0125787 A1 | 5/2008 | Doubler et al. |
| 2007/0233075 A1 | 10/2007 | Dawson | | 2008/0132952 A1 | 6/2008 | Malandain et al. |
| 2007/0233078 A1 | 10/2007 | Justis et al. | | 2008/0140075 A1 | 6/2008 | Ensign et al. |
| 2007/0233080 A1 | 10/2007 | Na et al. | | 2008/0140076 A1 | 6/2008 | Jackson |
| 2007/0233085 A1 | 10/2007 | Biedermann et al. | | 2008/0140133 A1 | 6/2008 | Allard et al. |
| 2007/0233086 A1 | 10/2007 | Harms et al. | | 2008/0147122 A1 | 6/2008 | Jackson |
| 2007/0233087 A1 | 10/2007 | Schlapfer | | 2008/0154307 A1 | 6/2008 | Colleran et al. |
| 2007/0233092 A1 | 10/2007 | Falahee | | 2008/0161854 A1 | 7/2008 | Bae et al. |
| 2007/0233094 A1 | 10/2007 | Colleran et al. | | 2008/0161859 A1 | 7/2008 | Nilsson |
| 2007/0233095 A1 | 10/2007 | Schlaepfer | | 2008/0161863 A1 | 7/2008 | Arnold et al. |
| 2007/0250061 A1 | 10/2007 | Chin et al. | | 2008/0167687 A1 | 7/2008 | Colleran et al. |

| | | | | | | |
|---|---|---|---|---|---|---|
| 2008/0177316 A1 | 7/2008 | Bergeronk et al. | | 2009/0198281 A1 | 8/2009 | Rice et al. |
| 2008/0177317 A1 | 7/2008 | Jackson | | 2009/0228045 A1 | 9/2009 | Hayes et al. |
| 2008/0177319 A1 | 7/2008 | Schwab | | 2009/0240286 A1 | 9/2009 | Friedrich et al. |
| 2008/0177321 A1 | 7/2008 | Drewry et al. | | 2009/0240287 A1 | 9/2009 | Cunliffe et al. |
| 2008/0177322 A1 | 7/2008 | Davis et al. | | 2009/0248075 A1 | 10/2009 | Ogilvie et al. |
| 2008/0177327 A1 | 7/2008 | Malandain et al. | | 2009/0248077 A1 | 10/2009 | Johns |
| 2008/0183212 A1 | 7/2008 | Veldman et al. | | 2009/0248081 A1 | 10/2009 | LeHuec et al. |
| 2008/0183213 A1 | 7/2008 | Veldman et al. | | 2009/0248083 A1 | 10/2009 | Patterson et al. |
| 2008/0183215 A1 | 7/2008 | Altarac et al. | | 2009/0248088 A1 | 10/2009 | Biedermann |
| 2008/0183216 A1 | 7/2008 | Jackson | | 2009/0254123 A1 | 10/2009 | Pafford et al. |
| 2008/0183223 A1 | 7/2008 | Jeon et al. | | 2009/0259257 A1 | 10/2009 | Prevost |
| 2008/0195100 A1 | 8/2008 | Capote et al. | | 2009/0259258 A1 | 10/2009 | Perez-Cruet et al. |
| 2008/0195153 A1 | 8/2008 | Thompson | | 2009/0270917 A1 | 10/2009 | Boehm |
| 2008/0215095 A1 | 9/2008 | Biedermann et al. | | 2009/0270920 A1 | 10/2009 | Douget et al. |
| 2008/0221620 A1 | 9/2008 | Krause | | 2009/0270921 A1 | 10/2009 | Krause |
| 2008/0221692 A1 | 9/2008 | Zucherman et al. | | 2009/0270922 A1 | 10/2009 | Biedermann et al. |
| 2008/0228227 A1 | 9/2008 | Brown et al. | | 2009/0275981 A1 | 11/2009 | Abdelgany et al. |
| 2008/0228229 A1 | 9/2008 | Walder et al. | | 2009/0275983 A1 | 11/2009 | Veldman et al. |
| 2008/0234691 A1 | 9/2008 | Schwab | | 2009/0275986 A1 | 11/2009 | Prevost et al. |
| 2008/0234734 A1 | 9/2008 | Wabler et al. | | 2009/0281572 A1 | 11/2009 | White |
| 2008/0234736 A1 | 9/2008 | Trieu et al. | | 2009/0281573 A1 | 11/2009 | Biedermann et al. |
| 2008/0234737 A1 | 9/2008 | Bosehert | | 2009/0287250 A1 | 11/2009 | Molz, IV et al. |
| 2008/0234739 A1 | 9/2008 | Hudgins et al. | | 2009/0287251 A1 | 11/2009 | Bae et al. |
| 2008/0234744 A1 | 9/2008 | Zylber et al. | | 2009/0287252 A1 | 11/2009 | Marik et al. |
| 2008/0234746 A1 | 9/2008 | Jahng et al. | | 2009/0299411 A1 | 12/2009 | Laskowitz et al. |
| 2008/0243188 A1 | 10/2008 | Walder | | 2009/0318968 A1 | 12/2009 | Duggal et al. |
| 2008/0255617 A1 | 10/2008 | Cho et al. | | 2009/0326582 A1 | 12/2009 | Songer et al. |
| 2008/0262546 A1 | 10/2008 | Calvosa et al. | | 2009/0326583 A1 | 12/2009 | Moumene et al. |
| 2008/0262548 A1 | 10/2008 | Lange et al. | | 2010/0010544 A1 | 1/2010 | Fallin et al. |
| 2008/0262552 A1 | 10/2008 | Kim | | 2010/0030271 A1 | 2/2010 | Winslow et al. |
| 2008/0262554 A1 | 10/2008 | Hayes et al. | | 2010/0036420 A1 | 2/2010 | Kalfas et al. |
| 2008/0269804 A1 | 10/2008 | Holt | | 2010/0036422 A1 | 2/2010 | Flynn et al. |
| 2008/0275504 A1 | 11/2008 | Bonin et al. | | 2010/0036423 A1 | 2/2010 | Hayes et al. |
| 2008/0287994 A1 | 11/2008 | Perez-Cruet et al. | | 2010/0036424 A1 | 2/2010 | Fielding et al. |
| 2008/0300630 A1 | 12/2008 | Bohnema et al. | | 2010/0036425 A1 | 2/2010 | Barrus et al. |
| 2008/0300633 A1 | 12/2008 | Jackson | | 2010/0042155 A1 | 2/2010 | Biedermann et al. |
| 2008/0306528 A1 | 12/2008 | Winslow et al. | | 2010/0042156 A1 | 2/2010 | Harms et al. |
| 2008/0306533 A1 | 12/2008 | Winslow et al. | | 2010/0049254 A1 | 2/2010 | Biedermann et al. |
| 2008/0306536 A1 | 12/2008 | Frig et al. | | 2010/0057125 A1 | 3/2010 | Viker |
| 2008/0306539 A1 | 12/2008 | Cain et al. | | 2010/0057126 A1 | 3/2010 | Hestad |
| 2008/0306540 A1 | 12/2008 | Mitchell et al. | | 2010/0063544 A1 | 3/2010 | Butler |
| 2008/0306543 A1 | 12/2008 | Cain et al. | | 2010/0063545 A1 | 3/2010 | Richelsoph |
| 2008/0306545 A1 | 12/2008 | Winslow | | 2010/0063547 A1 | 3/2010 | Morin et al. |
| 2008/0312694 A1 | 12/2008 | Peterman et al. | | 2010/0063551 A1 | 3/2010 | Richelsoph |
| 2009/0005817 A1 | 1/2009 | Friedrich et al. | | 2010/0069964 A1 | 3/2010 | Lechmann |
| 2009/0018583 A1 | 1/2009 | Song et al. | | 2010/0082071 A1 | 4/2010 | Moumene et al. |
| 2009/0024165 A1 | 1/2009 | Ferree | | 2010/0087858 A1 | 4/2010 | Abdou |
| 2009/0024169 A1 | 1/2009 | Triplett et al. | | 2010/0087862 A1 | 4/2010 | Biedermann et al. |
| 2009/0030464 A1 | 1/2009 | Hestad et al. | | 2010/0087863 A1 | 4/2010 | Biedermann et al. |
| 2009/0030465 A1 | 1/2009 | Altarac et al. | | 2010/0087865 A1 | 4/2010 | Biedermann et al. |
| 2009/0048631 A1 | 2/2009 | Bhatnagar et al. | | 2010/0094348 A1 | 4/2010 | Biedermann et al. |
| 2009/0054932 A1 | 2/2009 | Butler et al. | | | | |
| 2009/0069849 A1 | 3/2009 | Oh et al. | | \multicolumn{3}{c}{FOREIGN PATENT DOCUMENTS} | | |
| 2009/0076549 A1 | 3/2009 | Lim et al. | | | | |
| 2009/0082815 A1 | 3/2009 | Zylber et al. | | DE | 9202745 | 4/1992 |
| 2009/0088799 A1 | 4/2009 | Yeh | | DE | 4239716 | 8/1994 |
| 2009/0088803 A1 | 4/2009 | Justis et al. | | DE | 4425392 | 11/1995 |
| 2009/0093820 A1 | 4/2009 | Trieu et al. | | DE | 19507141 | 9/1996 |
| 2009/0093843 A1 | 4/2009 | Lemoine et al. | | DE | 19509141 | 9/1996 |
| 2009/0093845 A1 | 4/2009 | Hestad et al. | | DE | 19509331 | 9/1996 |
| 2009/0093846 A1 | 4/2009 | Hestad et al. | | DE | 29806563 | 7/1998 |
| 2009/0099606 A1 | 4/2009 | Hestad et al. | | DE | 29810798 | 12/1999 |
| 2009/0099607 A1 | 4/2009 | Fallin et al. | | DE | 19951145 | 5/2001 |
| 2009/0099608 A1 | 4/2009 | Szczesny | | DE | 10236691 | 2/2004 |
| 2009/0105760 A1 | 4/2009 | Frey | | DE | 102007055745 | 7/2008 |
| 2009/0112265 A1 | 4/2009 | Hudgins et al. | | EP | 0667127 | 8/1995 |
| 2009/0112266 A1 | 4/2009 | Weng et al. | | EP | 0669109 | 8/1995 |
| 2009/0112267 A1 | 4/2009 | Atkinson et al. | | EP | 0677277 | 10/1995 |
| 2009/0118767 A1 | 5/2009 | Hestad et al. | | EP | 0885598 | 12/1998 |
| 2009/0125063 A1 | 5/2009 | Panjabi | | EP | 1121902 | 8/2001 |
| 2009/0131981 A1 | 5/2009 | White | | EP | 1190678 | 3/2002 |
| 2009/0138052 A1 | 5/2009 | Biedermann et al. | | EP | 1570795 | 2/2005 |
| 2009/0149885 A1 | 6/2009 | Durwood et al. | | EP | 1579816 | 9/2005 |
| 2009/0163953 A1 | 6/2009 | Biedermann et al. | | EP | 1634537 | 3/2006 |
| 2009/0163954 A1 | 6/2009 | Kwak | | FR | 2717370 | 9/1995 |
| 2009/0163955 A1 | 6/2009 | Moumene et al. | | FR | 2718946 | 10/1995 |
| 2009/0171395 A1 | 7/2009 | Jeon et al. | | FR | 2729291 | 7/1996 |
| 2009/0177232 A1 | 7/2009 | Kiester | | FR | 2796545 | 1/2001 |
| 2009/0192548 A1 | 7/2009 | Jeon et al. | | FR | 2799949 | 4/2001 |
| | | | | FR | 2814936 | 4/2002 |

| | | |
|---|---|---|
| FR | 2856578 | 6/2003 |
| FR | 2865373 | 1/2004 |
| FR | 2865375 | 1/2004 |
| FR | 2865377 | 1/2004 |
| FR | 2846223 | 4/2004 |
| FR | 2857850 | 4/2004 |
| FR | 2865378 | 10/2004 |
| GB | 1519139 | 7/1978 |
| GB | 2365345 | 2/2002 |
| GB | 2382304 | 5/2003 |
| JP | 10277070 | 10/1998 |
| JP | 2000325358 | 3/2000 |
| SU | 313538 | 10/1971 |
| WO | WO92/03100 | 3/1992 |
| WO | WO94/10927 | 5/1994 |
| WO | WO94/26191 | 11/1994 |
| WO | WO96/41582 | 12/1996 |
| WO | WO01/28436 | 4/2001 |
| WO | WO01/45576 | 6/2001 |
| WO | WO02/054966 | 7/2002 |
| WO | WO02/102259 | 12/2002 |
| WO | WO03/026523 | 4/2003 |
| WO | WO03/068088 | 8/2003 |
| WO | WO2004/041100 | 5/2004 |
| WO | WO2004/075778 | 9/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/013839 | 2/2005 |
| WO | WO2005/020829 | 3/2005 |
| WO | WO2005/065374 | 7/2005 |
| WO | WO2005/065375 | 7/2005 |
| WO | WO2005/072632 | 8/2005 |
| WO | WO2005/082262 | 9/2005 |
| WO | WO2005/099400 | 10/2005 |
| WO | WO2005/104969 | 11/2005 |
| WO | WO2006/005198 | 1/2006 |
| WO | WO2006/012088 | 2/2006 |
| WO | WO2006/017616 | 2/2006 |
| WO | WO2006/020530 | 2/2006 |
| WO | WO2006/028537 | 3/2006 |
| WO | WO2006/045094 | 4/2006 |
| WO | WO2006/086537 | 8/2006 |
| WO | WO2006/116662 | 11/2006 |
| WO | WO2006/119241 | 11/2006 |
| WO | WO2007/002409 | 1/2007 |
| WO | WO2007/118045 | 10/2007 |
| WO | WO2007/124222 | 11/2007 |
| WO | WO2007/130835 | 11/2007 |
| WO | WO2007/130840 | 11/2007 |
| WO | WO2007/130941 | 11/2007 |
| WO | WO2008/045210 | 4/2008 |
| WO | WO2008/069420 | 6/2008 |
| WO | WO2008/088990 | 7/2008 |
| WO | WO2008/089075 | 7/2008 |
| WO | WO2008/140756 | 11/2008 |
| WO | WO2009/036541 | 3/2009 |
| WO | WO2010/018316 | 2/2010 |
| WO | WO2010/018317 | 2/2010 |
| WO | WO2010/019704 | 2/2010 |
| WO | WO2010/019857 | 2/2010 |

OTHER PUBLICATIONS

Brochure of Spinal Concepts, an Abbott Laboratories Company, *Pathfinder, Minimally Invasive Pedicle Fixation System*, Publication Date: Nov. 2003.
Brochure of Spinal Concepts, Surgical Technique, *InCompass, Thoracolumbar Fixation System*, Publication Date: Oct. 2003.
Brochure of SpineLine, Current Concepts, *Minimally Invasive Posterior Spinal Decompression and Fusion Procedures*, Publication Date: Sep./Oct. 2003.
Brochure of Sofamor Danek the Spine Specialist, TSRH, *Pedicle Screw Spinal System*, Publication Date: Jan. 23, 1995.
Brochure of Spinal Concepts, InCompass, Thoracolumbar Fixation System, Publication Date: Oct. 2003.
Brochure of Zimmer Spine, Inc., Dynesys® LIS Less Invasive Surgery, The Dynamic Stabilization System, Publication Date: 2005.
Claris Instrumentation Brochure, G Med, pub. 1997.
EBI Omega 21 Brochure, EBI Spine Systems, pub. 1999.
SDRS Surgical Dynamics Rod System Brochure, Surgical Dynamics, pub. 1998-99.
Spine, Lipcott, Williams & Wilkins, Inc. vol. 24, No. 15, p. 1495.
The Rod Plate System Brochure, Stryker Howmedica Osteonics, pub. Oct. 1999.
Versalok Low Back Fixation System Brochure, Wright Medical Technology, Inc., pub. 1997.
VLS System Variable Locking Screw Brochure, Interpore Cross International, 1999.

\* cited by examiner

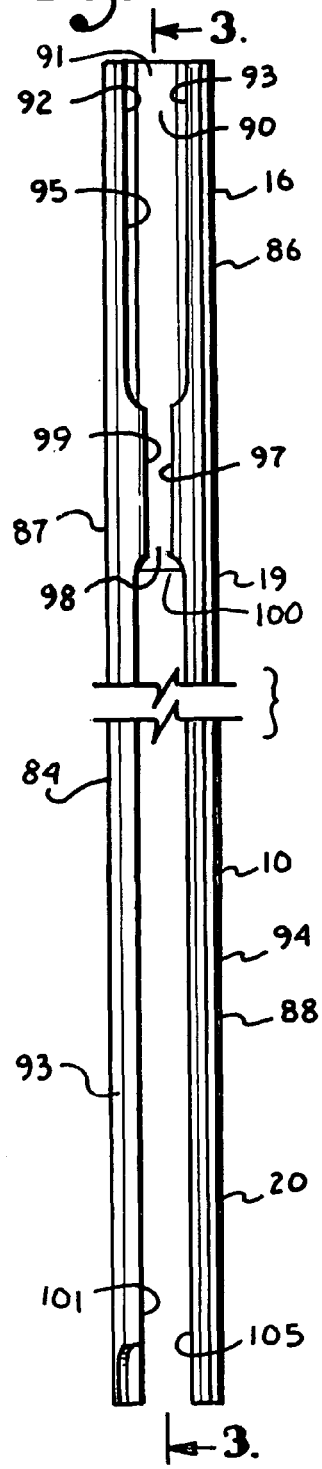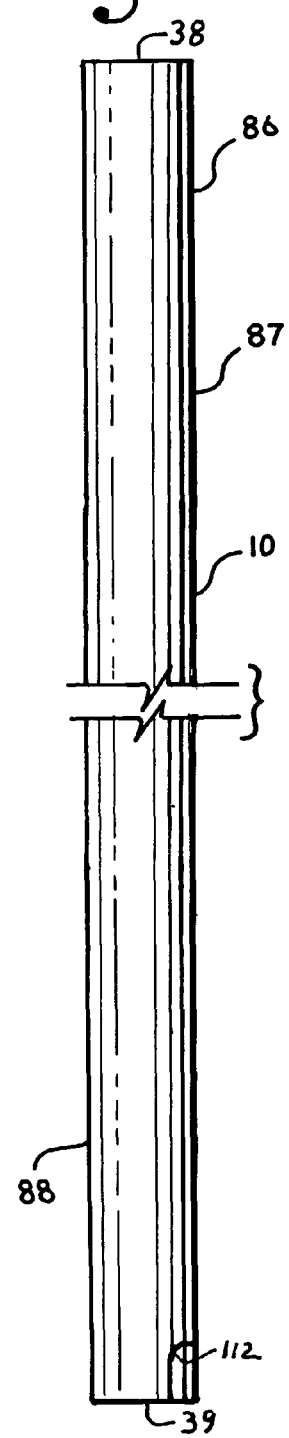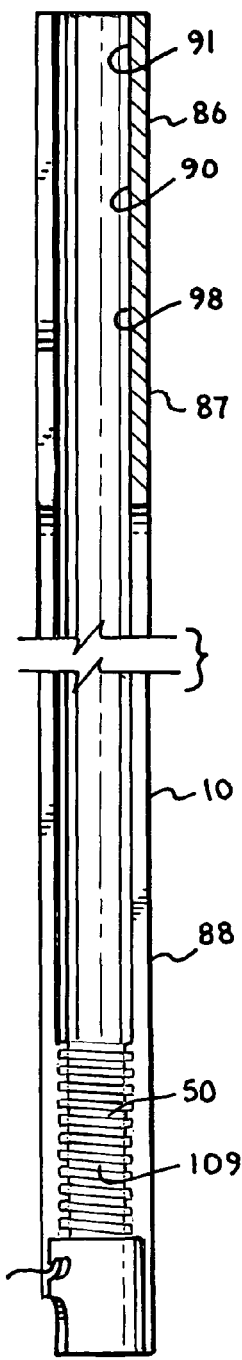

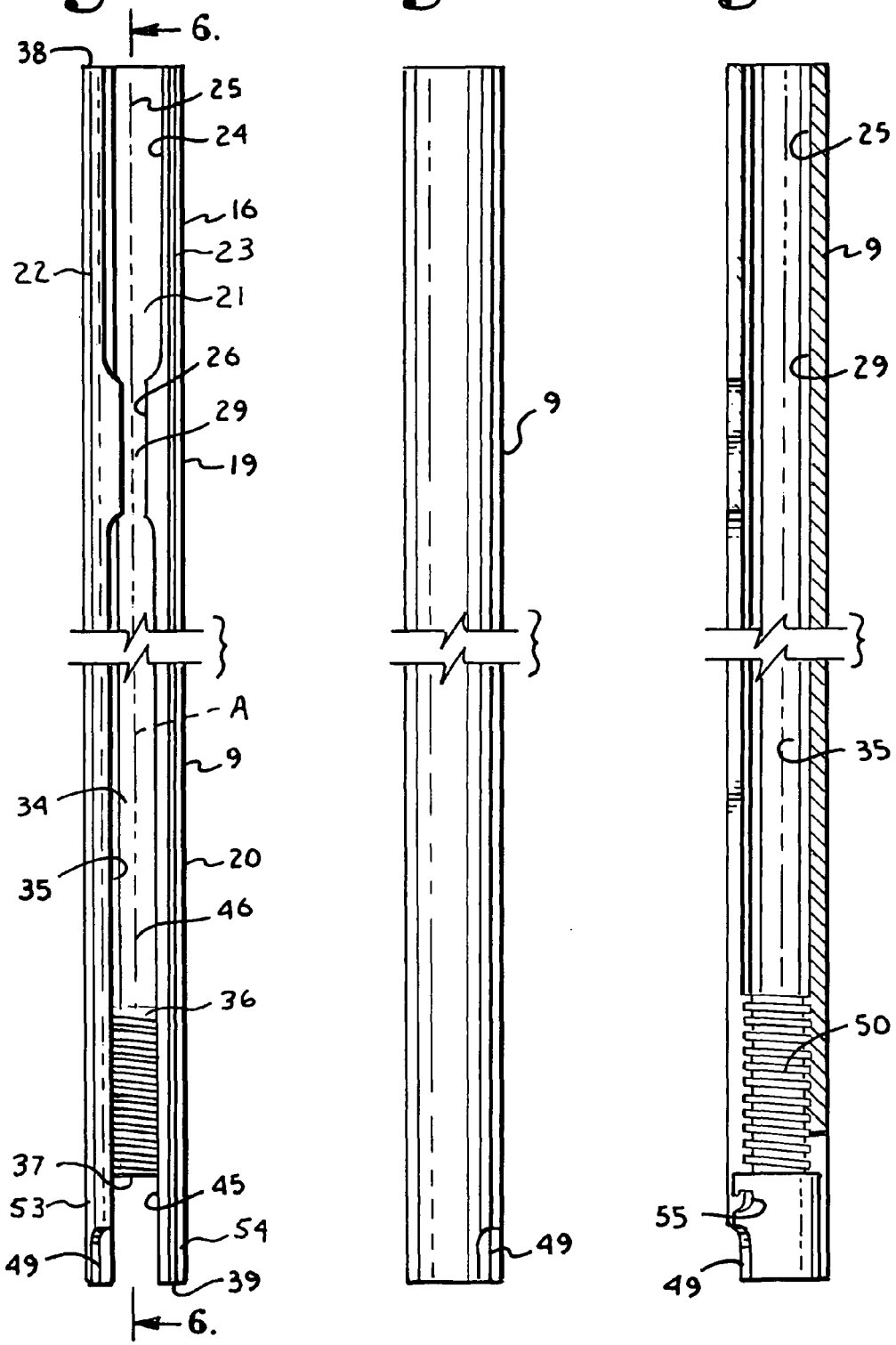

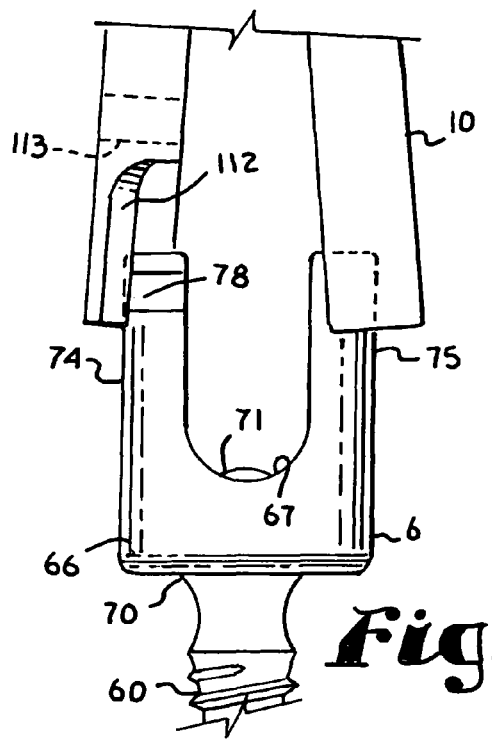
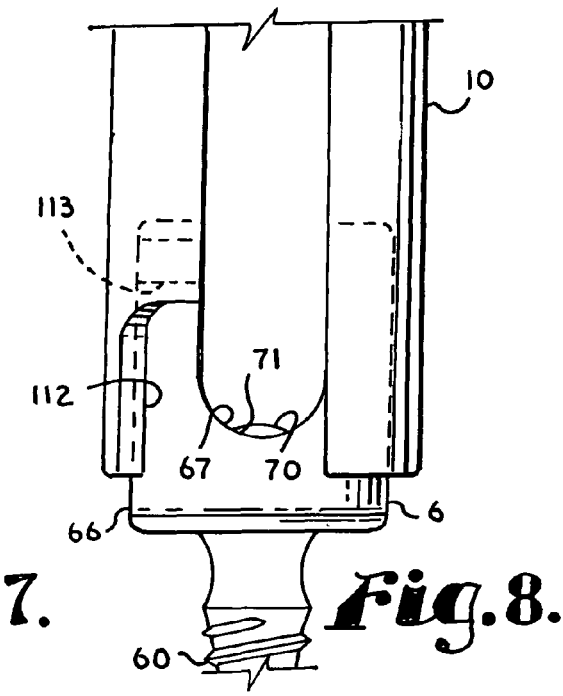
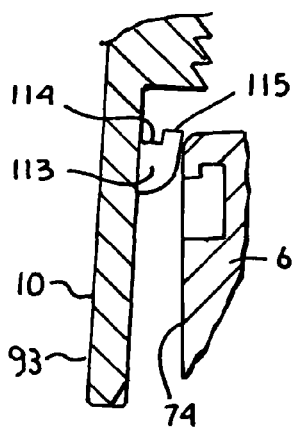
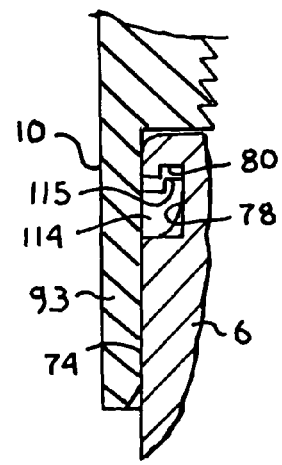
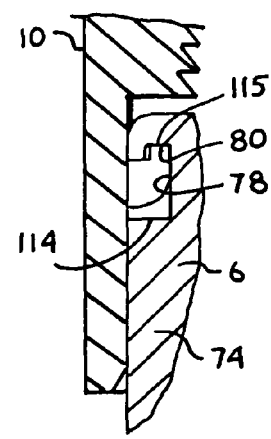

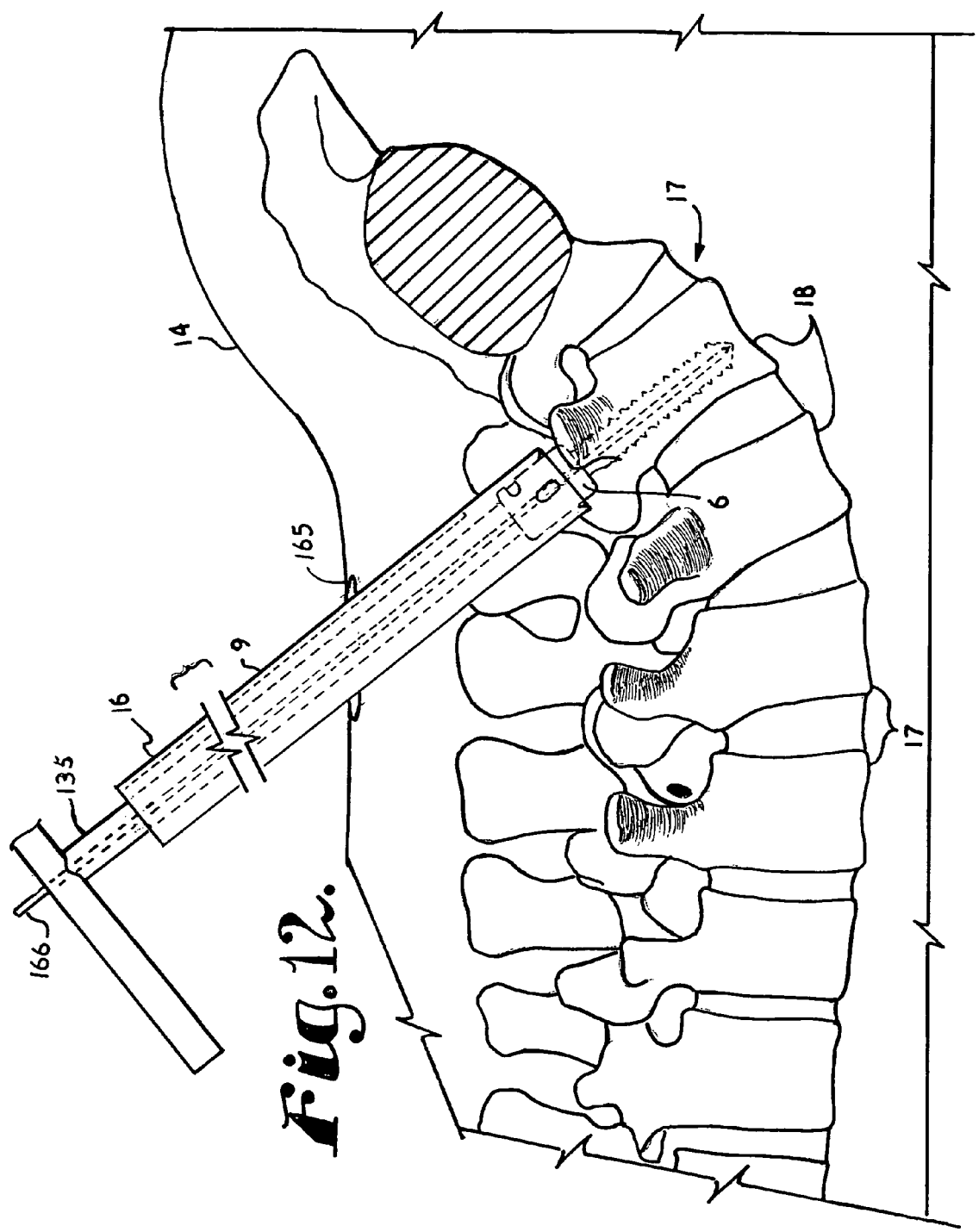

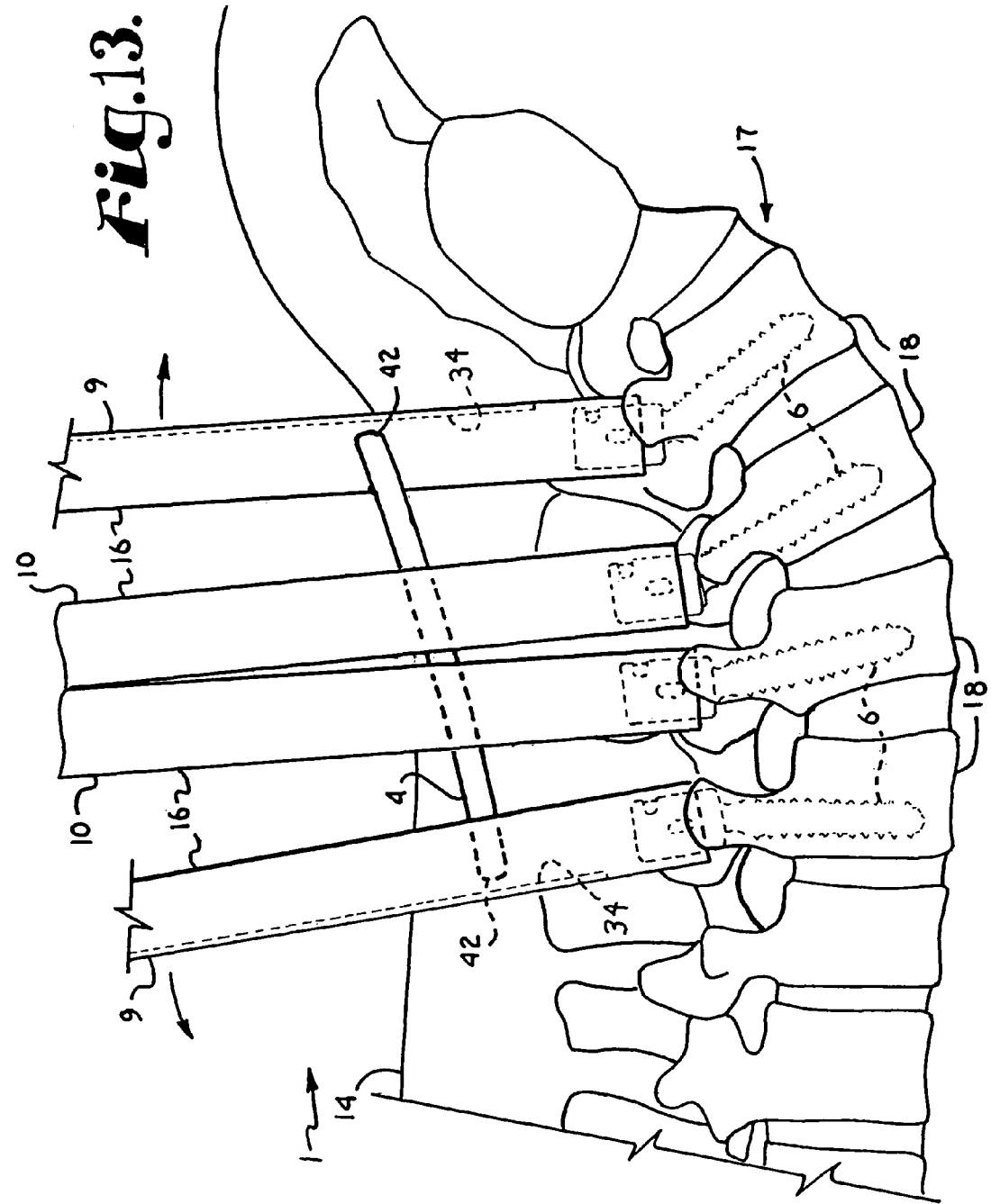

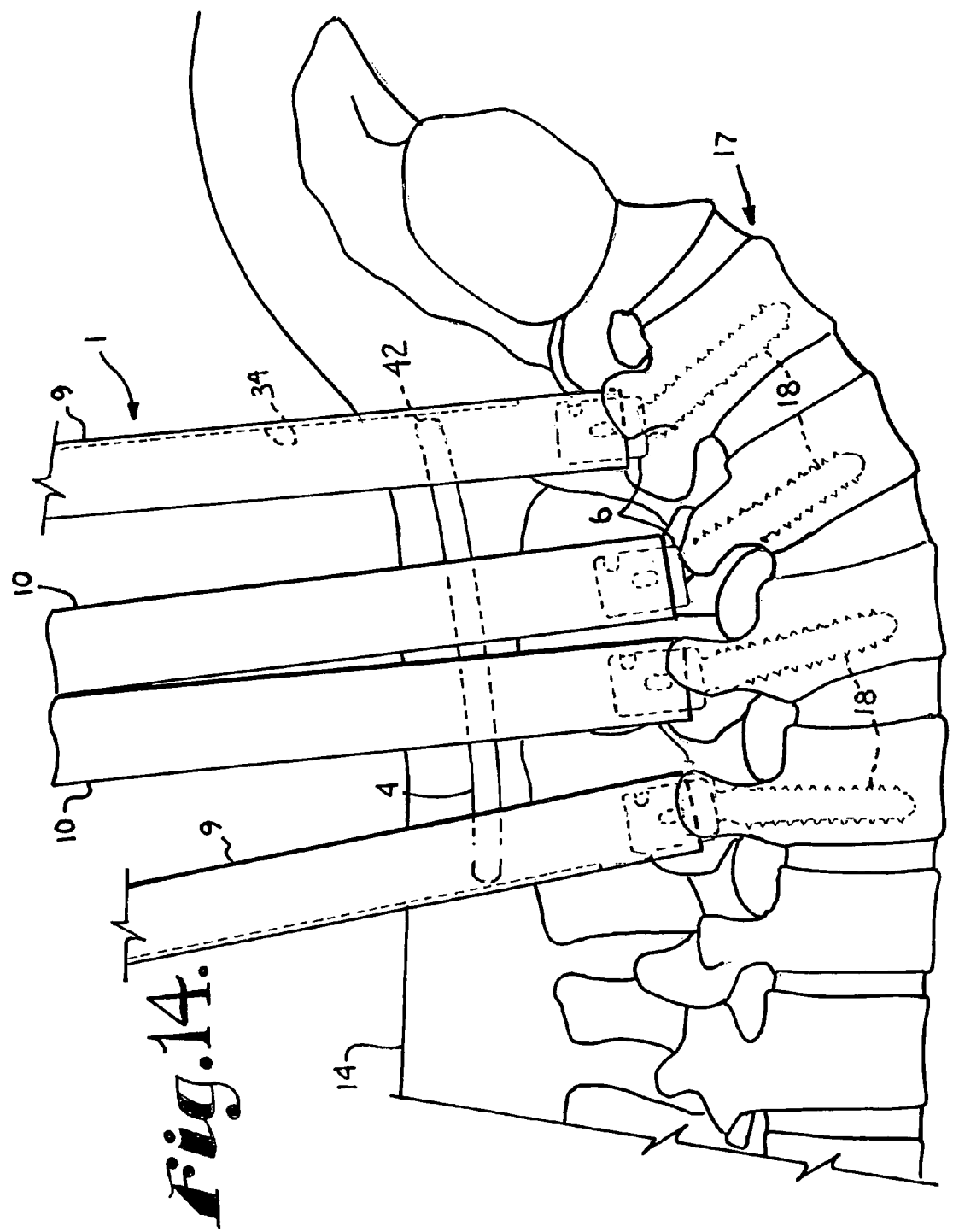

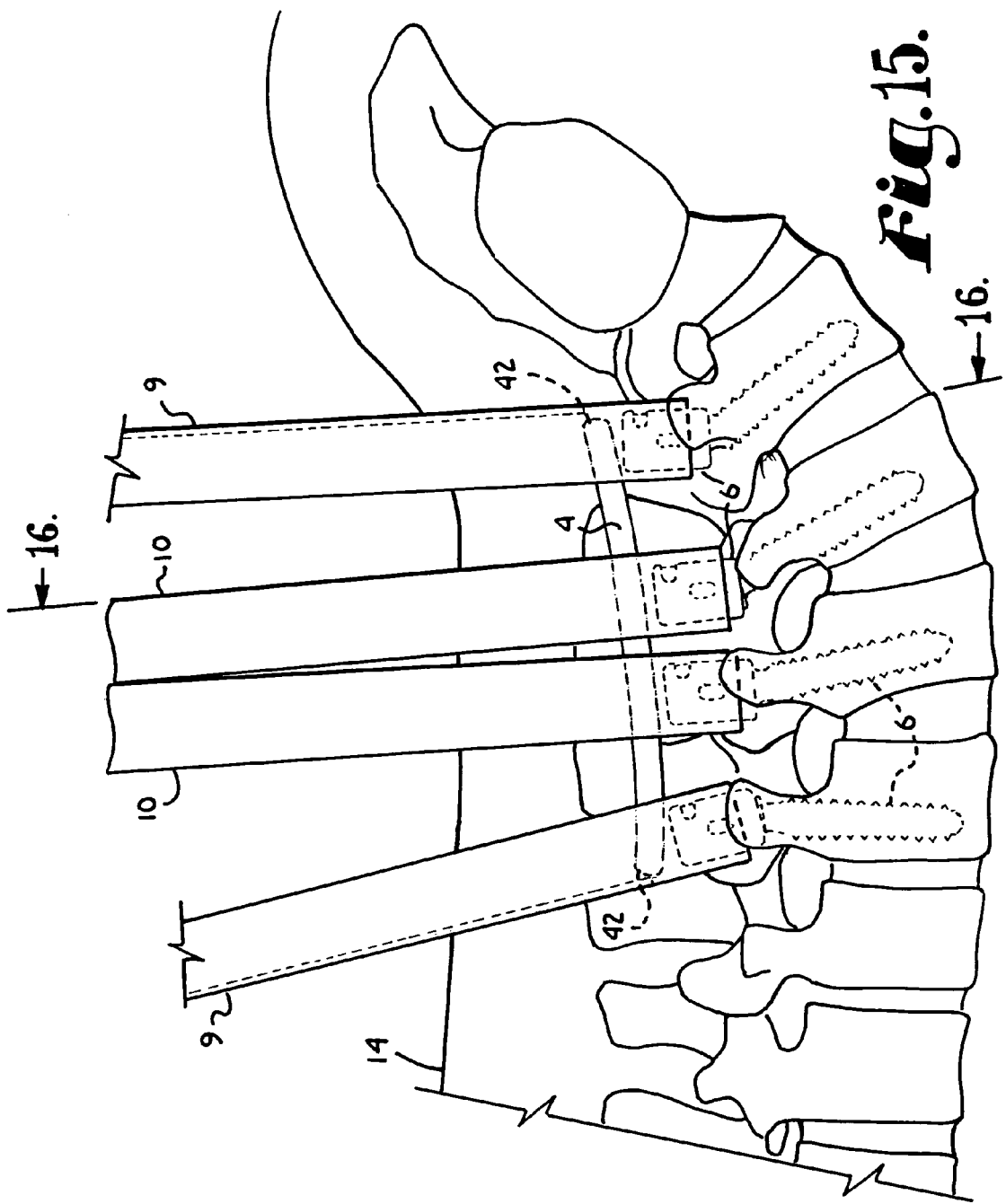

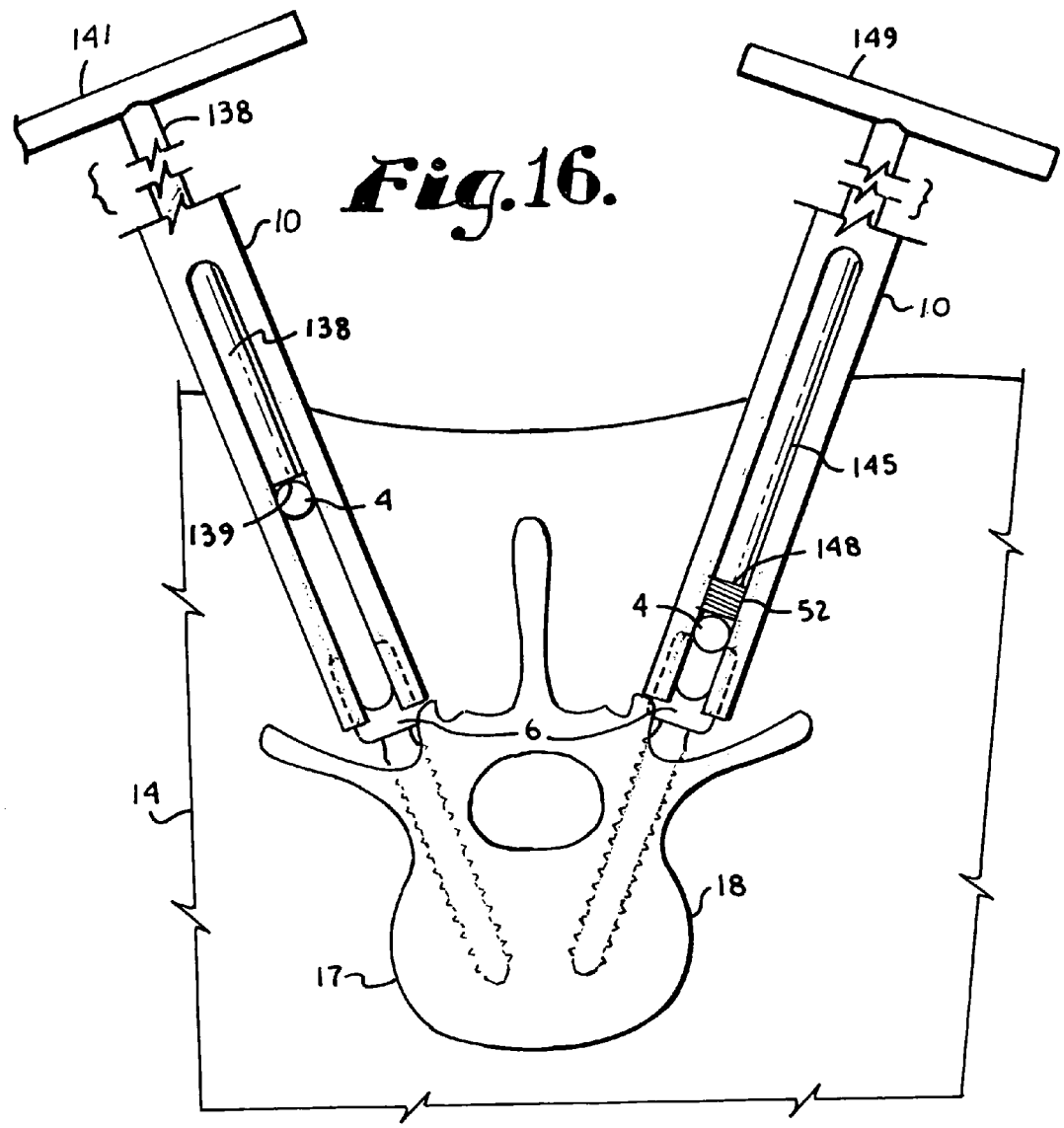

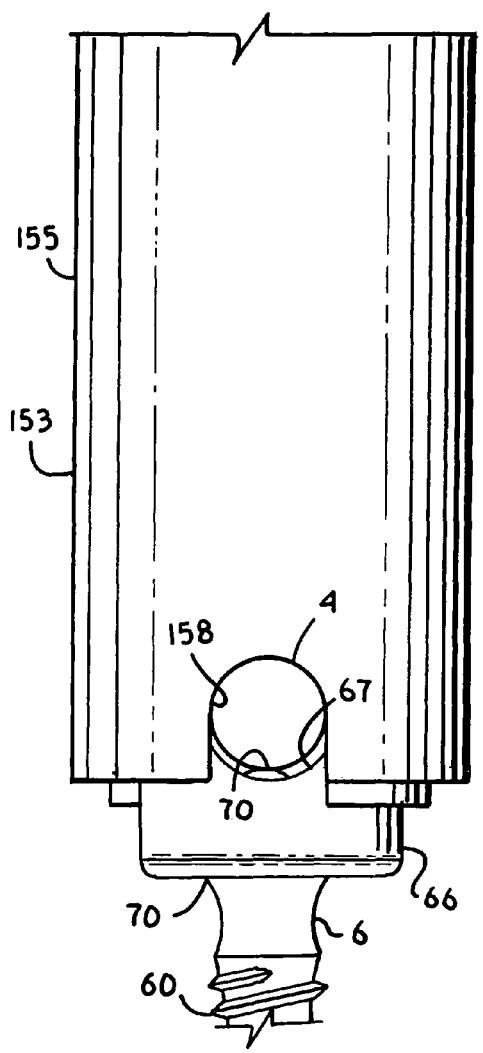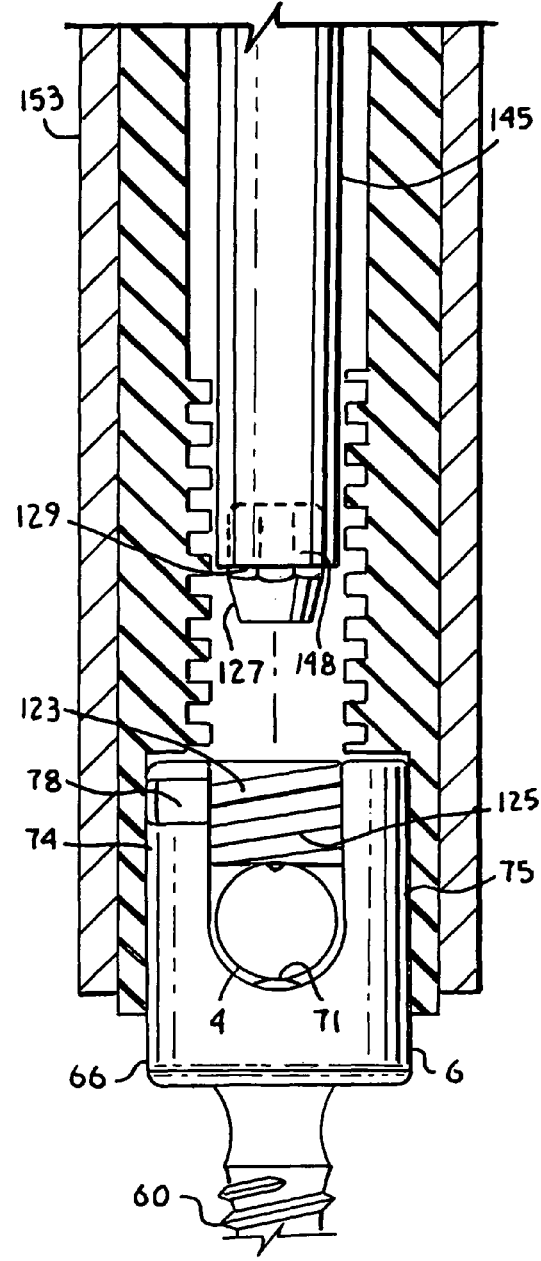

ORTHOPEDIC IMPLANT ROD REDUCTION TOOL SET AND METHOD

CROSS REFERENCE TO RELATED APPLICATIONS

This application is a continuation of U.S. application Ser. No. 11/502,926, filed Aug. 11, 2006 and also a divisional continuation of U.S. application Ser. No. 10/789,149, filed Feb. 27, 2004, now U.S. Pat. No. 7,160,300.

BACKGROUND OF THE INVENTION

The present invention relates to apparatuses and methods for use in performing spinal surgery and, in particular, to tools and methods of using such tools, especially for percutaneously implanting a rod for spinal support and alignment using minimally invasive techniques.

For many years, spinal osteosynthesis apparatuses have been utilized to correct spinal deformities, injuries or disease. In such procedures, elongate rods are surgically attached to vertebrae of the spine to provide support and/or to reposition certain vertebrae. Such rods are secured to vertebrae utilizing bone screws and other implants.

Surgical techniques and bone screws have improved; however, in order to reduce the impact of such surgery on the patient, it has been desirable for such implants to be inserted percutaneously or with surgical techniques that are minimally invasive to the body of the patient. This presents a problem with implantation of rods that are elongate and have historically required a long incision and open wound in order to provide for the length of the rod and the space required for the surgeon's hands to manipulate the rod, implants and insertion tools used with the rod. Consequently, it has been desirable to develop apparatuses and techniques that allow for the insertion of bone screws, the insertion and reduction of a rod and the securing of the rod to the bone screws with significantly reduced invasion into the body of the patient and with minimal incision size in the skin over the operational site.

SUMMARY OF THE INVENTION

A set of tools is provided for percutaneously implanting a spinal rod in a patient. The tools include a pair of end guide tools that have channels sized to receive opposite ends of such a rod and allow sliding of the rod along the channel so as to guide ends of the rod into opposed end bone screw-heads to which the end guide tools are attached. Intermediate guide tools are also attached to bone screw-heads between the end bone screws and are slotted to guide the rod to respective bone screws attached to the intermediate guide tools.

The guide tools also include lower attachment structure to allow the guide tools to be easily and quickly secured to mating structure on a respective bone screw-head, and to be easily removed from the bone screw by manual rotation of a handle of the tools exterior of the patient, after which the guide tool is withdrawn from the patient. The intermediate guide tools have a snap-on and twist-off association with an associated intermediate bone screw and the end guide tools have a twist-on and twist-off association with respective end bone screws. In certain embodiments, other attachment structure may be used.

Each of the guide tools also includes an internal first lower guide and advancement structure that functions in cooperation with an internal second guide and advancement structure within the bone screw head and also with external helical wound thread or locking flange form mating structure on a bone screw closure top for closing the head of the bone screw, so as to be able to load the closure top though a top-to-bottom passageway in the guide tool and rotate the closure top with a closure top installation tool. Beneath the surface of the skin, the closure top is partially surrounded by the guide tool as it is directed to the bone screw. Clockwise rotation of the closure top in the region of the lower guide and advancement structure engages the closure top therewith and produces mechanical advantage that causes the closure top to be driven against the rod as it advances thereby urging the rod into the head of a respective bone screw. The closure top is driven and advanced by rotation of the closure top by the closure top installation tool and transferred or passed from the first guide and advancement structure in the guide tool to the second guide and advancement structure in the bone screw without losing mechanical advantage and while continually applying downward pressure on the rod, so as to drive the closure top downward and against the rod and so as to bias the rod into the head of the bone screw where it is captured by the closure top and locked in position.

OBJECTS AND ADVANTAGES OF THE INVENTION

Therefore, the objects of the present invention are: to provide a set of tools for implanting a spinal rod for support or alignment along a human spine with minimal surgical invasion of the patient; to provide such a set of tools including a pair of end tool guides for slidably guiding opposed ends of the rod toward end bone screws attached to the end guide tools; to provide such a set of tools including intermediate guide tools for each intermediate bone screw that guide the rod in slots therethrough to respective bone screws; to provide such a set of tools including rod pusher and closure top installation tools for assisting in securing the rod in the bone screws; to provide such a set of tools where the end guide tools include a longitudinal channel extending upwardly from near a bottom thereof to slidingly receive and guide ends of the rod toward associated end bone screws; to provide such a set of tools wherein the guide tools are easily attached to and disengaged from the bone screws; to provide such a set of tools wherein each guide tool includes a first guide and advancement structure near the bottom thereof that receives thread or locking flange mating structure on the closure top and advances the closure top upon rotation of the closure top to urge the rod downwardly; to provide such a set of tools wherein the guide tool first guide and advancement structure acts cooperatively with a second guide and advancement structure on the bone screw so as to transfer the closure top upon rotation thereof from the guide tool to the bone screw while continuously applying pressure to the rod and thereafter further advance the closure top to urge the rod into a seated position in the bone screw; to provide such a set of tools wherein the guide tools easily attach to and disengage from the bone screws by manual manipulation of the surgeon outside the patient's skin; to provide a method of implanting a rod into a patient with minimal surgical invasion of the patient; to provide such a method utilizing the previously described tools for percutaneous implantation of such a rod; to provide such a method wherein end guide tools are utilized to receive opposite ends of a rod and guide the rod ends in the guide tool channels through manipulation of the guide tools and use of rod pusher tools; to provide such a method wherein intermediate guide tools are utilized to guide intermediate locations along the rod to respective intermediate bone screws; to provide such a method wherein guide and advancement structure near the bottoms of the guide tools, on the bone screws and on the closure tops are utilized to pass the closure top under rotation and with driving force between the guide tools and the bone screws and to drive the rod into a seating position in the bone screw; and to provide such a set of tools and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary front elevational view of an intermediate guide tool in accordance with the present invention.

FIG. 2 is a fragmentary side elevational view of the intermediate guide tool.

FIG. 3 is a fragmentary cross sectional view of the intermediate guide tool, taken along line 3-3 of FIG. 1.

FIG. 4 is a fragmentary front elevational view of an end guide tool.

FIG. 5 is a fragmentary side elevational view of the end guide tool.

FIG. 6 is a cross sectional view of the end guide tool, taken along line 6-6 of FIG. 4.

FIG. 7 is an enlarged and fragmentary front elevational view showing snap-on installation of the intermediate guide tool on a polyaxial bone screw head.

FIG. 8 is an enlarged and fragmentary front elevational view showing the intermediate guide tool installed on the bone screw head.

FIG. 9 is a fragmentary and cross-sectional view showing an early stage of the snap on installation of the intermediate guide tool on the bone screw head.

FIG. 10 is a fragmentary and cross-sectional view showing a later stage of installation of the intermediate guide tool on the bone screw head.

FIG. 11 is a fragmentary and cross-sectional view showing the intermediate guide tool installed on the bone screw head.

FIG. 12 is a partial and generally schematic view of a patient's spine with the end guide tool in conjunction with a bone screw installation tool, at the end of a process of installing a bone screw with attached end guide tool in a spinal vertebra.

FIG. 13 is a partial and generally schematic view of the spine with a pair of end guide tools and a pair of intermediate guide tools mounted on respective implanted bone screws and being utilized in an early stage of rod implantation to guide the rod toward the bone screws.

FIG. 14 is a view similar to FIG. 13 showing an intermediate stage of guiding the rod toward the bone screws.

FIG. 15 is a view similar to FIG. 13 showing a later intermediate stage of guiding the rod toward the bone screws.

FIG. 16 is a partial and generally schematic cross sectional view of the spine showing rods being implanted on opposite sides of the spine and with the rod on the left in an early stage of implanting while the rod on the right is in a later stage of implanting, taken along line 16-16 of FIG. 15.

FIG. 21 is a fragmentary and front elevational view of the antitorque tool being positioned so as to allow final torquing to a closure top in the bone screw.

FIG. 22 is an enlarged and fragmentary side view of the end guide tool, as shown in FIG. 21, in conjunction with the installation tool and antitorque tool with portions broken away to shown interior detail and with the closure top having just been installed and torqued in the bone screw so that a break away head of the closure top has been removed.

DETAILED DESCRIPTION OF THE INVENTION

Figure 17:
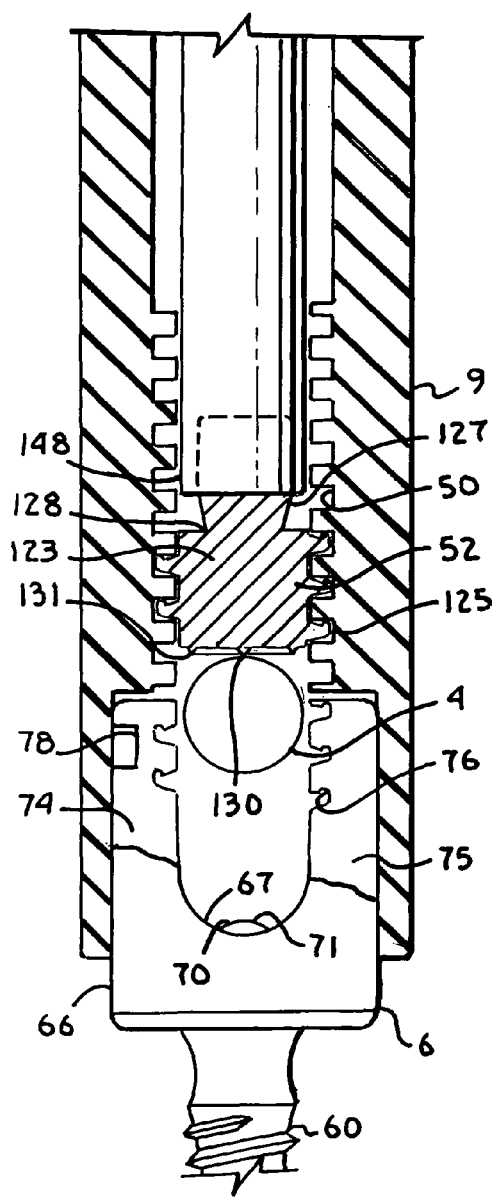
FIG. 17 is a cross-sectional view of an end guide tool, similar to FIG. 6, shown during installation of the rod and a closure top in the bone screw attached to the end guide tool.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally designates a tool set for use in installing an orthopedic spinal rod 4 into a set of bone screws 6 in accordance with the present invention.

The tool set 1 of the illustrated embodiment includes a pair of end guide tools 9 and a plurality of intermediate guide tools 10, which in the illustrated embodiment includes a pair of intermediate guide tools 10 on each side of a patient's spine 17, but which can include none, one or many intermediate guide tools 10 depending upon the particular application, so that one intermediate guide tool 10 is used for each intermediate bone screw 6 to which the rod 4 is to be attached. The bone screws 6 are implanted in the patent's spine 17 and, in particular, in vertebrae 18 along the spine 17. Rods 4 are often installed on both sides of the spine 17, as seen in FIG. 16, during the same procedure.

The end guide tool 9 is illustrated in FIGS. 4 through 6. In particular, each end guide tool 9 has an elongate body 14 that is sized and shaped to be sufficiently long to extend from implanted bone screws 6 through an exterior of a patient's skin 14 so as to provide an outwardly extending and upper handle portion 16 that allows and provides for gripping by a surgeon during procedures utilizing the tool set 1. Each of the end guides 9 include an intermediate portion 19 and a lower portion 20 along the length thereof. Each end guide tool 9 has a back wall 21 joining a pair of side walls 22 and 23.

More specifically, the upper portion 16 of each end guide tool 9 is generally channel shaped having a U-shaped cross-section, a C-shaped cross-section, a crescent shaped cross-section or the like in order to form an opening 24 that opens into and forms part of a channel 25 that opens radially to one side of the end guide tool 9 and defines the side to side opening 24 that is sufficiently wide to receive additional tools and/or a closure top, as will be discussed below. The intermediate portion 19 of each end guide also includes an outward facing channel 29 that has an opening 26 which is somewhat smaller than the opening 24 of the upper portion 16, such that the channel 29 is sized and shaped to receive certain tools, as described below. Finally, the end guide lower portion 20 also includes a groove or channel 34 opening radially outward and having a side-to-side width or opening 35 that is approximately the same size as the opening 26. The channel 34 has a rear web or wall 36 having a lower end 37. All of the channels 25, 29 and 34 communicate with one another and are aligned with one another so as to provide a continuous elongate interior passageway with an open side from near a top 38 to near a bottom 39 thereof. This passageway provides a continuous open path of non uniform cross-section radius from the top 38 to the bottom 39 thereof that is parallel to an elongate axis A of each end guide tool 9. As will be discussed later, each end guide tool channel 34 is especially sized and shaped to slidingly receive a respective end 42 of the rod 4 therein.

Near the end guide bottom 39 is a cut out 45 wherein a portion of the back wall 21 of the channel 34 is removed in order to provide a region having a size and shape to allow passage of a respective end 42 of the rod 4 therethrough. Also located near the end guide bottom 39 is a rod abutment recess 49 that is sized and shaped for the purpose of bridging the rod 4 when the end guide tool 9 is rotated for removal, as described below. The end guide tool 9 also receives a closure top 52, as will be described below. Still further, near the bottom 39 of each of the end guides 9 is a helical wound first guide and advancement structure 50 which may include conventional helical threads, helically wound square threads, or other guide and advancement structure to cooperate with equivalent or mateable structure within the bone screw heads 6 and on the closure top 52, as also described below. The lower free ends of the side walls 22 and 23 form spaced tangs or legs 53 and 54.

At the bottom 39 of each end guide tool 9 is a radially inward facing attachment structure 55 that includes a base 56 and an upperly and axially extending projection, flange or hook member 57 which will be described in conjunction with a bone screw 6 below.

Referring more specifically to the bone screw 6, each of the bone screws 6 includes a threaded shank 60 for screwing into and seating in a vertebra 18 that is part of the human spine 17, see FIG. 12. Each of the bone screws 6 also include a head 66 with a rod receiving channel 67 passing therethrough. Each of the bone screw shanks 60 includes an upper portion 70 that extends into the head 66 and is operationally secured therein, so that the head 66 is rotatable on the shank 60 until locked in position through engagement with the rod 4 under pressure. In particular, each shank upper portion 70 has an upwardly extending dome 71 that engages the rod 4, when the rod 4 is placed within an associated channel 67 so that as the rod 4 urges the dome 71 downwardly, the shank upper portion 70 frictionally locks the shank 60 in position in a fixed angular position relative to the head 66. Many different conventional bone screws where the head locks relative to the shank are well known in the art.

The present invention is not intended to be restricted to a particular type of bone screw. In the present embodiment, a polyaxial type bone screw 6 is utilized wherein the shank 60 is locked in position by direct contact with the rod 4. It is foreseen that tool set 1 of the present invention can be used with virtually any type of bone screw, including polyaxial bone screws of many different types wherein the head is locked relative to the shank by structure other than in the manner described in the illustrated embodiment.

Each bone screw head 66 has a pair of upstanding arms 74 and 75 with internal second guide and advancement structure 76 on the insides thereof. One of the arms 74 includes a circumferentionally located receiver 78 that comprises a lower slot 79 that extends partially circumferentially about the periphery of the arm 74 and ends in an upperwardly projecting but hidden recess 80. While the slot 79 is located on the arm 74 in the illustrated embodiment, a slot for this purpose could be located anywhere on the bone screw head 66. The slot 79 and recess 80 are sized, shaped and positioned so as to receive the attachment structure 55 of the end guides 9 therein. For greater detail, see the description below for the attachment structure associated with intermediate guide tools 10 and shown in FIGS. 10 and 11. The guide tool attachment structure 55 is sized and shaped to allow the attachment structure 55 to be received in the receiver 78 and locked therein by pulling the end guide tool 9 slightly axially upward relative to a respective bone screw 6. In order to disengage the guide tool 9 from the bone screw 6, the guide tool 9 is rotated 90 degrees counterclockwise from an attaching configuration, when viewing from the top so as to disengage the hook 57 from the recess 80 and so that the base 56 and hook 57 of the attachment structure 55 free to rotate above the rod 4 and closure top 52 and be released from the receiver 78. In this manner, end guide tools 9 twist off of respective bone screws 6 and in the particular illustrated embodiment the end guide tools 9 are also assembled on the bone screws 6 by the opposite twist on maneuver is the reverse of the twist off maneuver. In certain embodiments where there is enough flexibility in the legs 53 and 54, such that the legs 53 and 54 can be splayed radially outwardly at the bottom 39 thereof in the manner shown in FIG. 7, so the end guide tool 9 snaps-on over the bone screw 6, as will be described for the intermediate guide tools 10 below.

The unflexed space between the legs 53 and 54 that is equivalent to the width of the opening 35 is preferably substantially equivalent to the space between the bone screw arms 74 and 75 so that the channel 34 of the end guide tool 9 aligns with the channel 67 of the bone screw 6 when the end guide tool 9 is mounted on a respective bone screw 6. The recess 49 is sized, shaped and positioned so that when the rod 4 is located in the bone screws 6, the end guide tool 9 can rotate about axis A and the recess 49 allows the end guide tool 9 to straddle over the rod 4, thereby allowing the end guide tool 9 to twist relative to the bone screw 6 and free the attachment structure 55 from the receiver 78 and thereafter be removed after all procedures are complete, as described below.

Each of the intermediate guide tools 10 (see especially FIGS. 1 to 3) have a somewhat similar overall shape when compared to the end guide tools 9 in that both are preferably of the same axial length and width and also have much structure in common; however with certain differences as noted. Many of the structures of the intermediate guide tools 10 that are the same as the end guide tools 9 are given the same reference number and the above noted description applies to each such tool 9 or 10.

Each intermediate guide tool 10 has an overall elongate body 84 with an upper portion 86, an intermediate portion 87 and a lower portion 88. In the upper portion 86, the body 84 is generally C-shaped having a radially outward opening and elongate and axially extending channel 90 terminating in a web or rear wall 91 with side walls 92 and 93. The channel 90 has a front opening 95 that extends parallel to an axis of the body 84 and that is sized and shaped to receive tools and elements described below.

The intermediate portion 87 also includes an outwardly opening channel 97 with a rear web or wall 98 having a lower end 100 and a front opening 99 that is not as wide as the opening 95. The lower portion 88 includes two spaced side walls or legs 93 and 94 with an elongate and axially extending passthrough opening 101 between the legs 93 and 94 that extends more than half way along the intermediate tool 10 and near the intermediate portion 87. The legs 93 and 94 define between them a pass through and aligned slot 105 sized and shaped to slidingly receive the rod 6.

The lower portion 88 extends substantially axially along the intermediate guide tools 10 and preferably to the location in use where the intermediate guide tools 10 pass through the skin 14.

The bottom 39 of each intermediate guide tool 10 includes a helically wound but discontinuous square thread or first guide and advancement structure 109 that cooperates with the closure top 52, as described below. The lower end of each intermediate guide tool 10 also includes a cutout 112 and an attachment structure 113 similar to structure 55 of the same type described for each end guide tool 9.

The attachment structure 113 (see especially FIGS. 9 to 11) includes a body 114 with an upperwardly extending, projection, flange or hook member 115 that follows the inner curvature of the guide tool leg 93. The body 114 extends radially inward and is sized and shaped to mate with and set within the bone screw head receiver 78. The bone screw receiver 78 is sufficiently wide to simultaneously receive both the body 114 and hook member 115 in a radially inward direction, as is shown in the view in FIG. 10. The attachment structure 113 is then set by axially raising the guide tool 10 relative to the bone screw 6 so at least part of the hook member 115 is located in the recess 80 which secures the guide tool 10 (likewise guide tool 9) to a respective bone screw 6, as seen in FIG. 11. This locks the guide tool 10 to a respective bone screw 6 and prevents outward splaying of the leg 93. This is a snap-on type installation or assembly as seen in FIG. 7 where the leg 93 splays outward during initial placement of the guide tool 10 over the bone screw 6 and then returns to an unsplayed position when the attachment structure 113 seats in the receiver 78, as shown in FIG. 10. Alternatively, the guide tool 10 can be rotated approximately 90° about its axis A prior to joining with a respective bone screw 6, the attachment structure 113 lowered through the opening between the bone screw arms 74 and 75 and aligned with the bone screw receiver 78, after which the guide tool 10 is rotated back to the first position shown in FIG. 11 in a twist on type assembly. In some instances the guide tool 10 is rotated somewhat more or less than ninety degrees to make the necessary alignment for removal which depends on the specific construction of the parts.

Enclosure 52 closes between the spaced bone screw arms 74 and 75 to secure the rod 4 in the channel 67. The closure top 52 can be any of many different plug type closures. Preferably the closure top 52 has a cylindrical body 123 that has a helically wound mating guide and advancement structure 125. The guide and advance at structure 125 can be of any type, including V-type threads, buttress threads, reverse angle threads, or square threads. Preferably the guide and advancement structure 125 is a helically wound flange form that interlocks with a reciprocal flange form as part of the second guide and advancement structure 76 on the interior of the bone screw arms 74 and 75. A suitable locking guide and advancement structure of this type is disclosed in U.S. Pat. No. 6,726,689 from Ser. No. 10/236,123 which is incorporated herein by reference. The helical wound guide 50 and advancement structure in the bottom 39 of each of the guide tools 9 and 10 is sized and shaped to receive the mating guide and advancement structure 125 of the closure top 52 and align with the second guide and advancement structure 76 of the bone screw 6 to form a generally continuous helically wound pathway, but does not require locking between the closure top 52 and the tools 9 and 10, even when a locking flange form is utilized on the closure top 52. The illustrated structure 125 has a square form or a square thread type shape. The guide 50 allows the closure top 52 to be rotated and the surgeon to develop mechanical advantage to urge or drive the rod 4, while still outside the bone screw head 6, toward and into the bone screw head 66. This is especially helpful where the rod 4 is bent relative to the location of the vertebra 18 to which the rod 4 is to attach and is not easily placed in the bone screw head 66 without force and the mechanical advantage provided by the guide 50. In particular, the first guide and advancement structure 109 on each tool 9 and 10 is located and positioned to align with the second guide and advancement structure 76 on the insides of the bone screw arms 74 and 75, as seen in FIGS. 17 and 18 and pass the closure top 52 therebetween while allowing the closure top 52 to continue to rotate and to continuously apply force to the rod 4, so as to seat the rod 4 in the bone screw head 66.

Each closure top 52 also preferably includes a break off head 127 that breaks from the body 123 in a break off region 128 upon the application of a preselected torque, such as 95 inch-pounds. The break off head preferably has a hexagonal cross section faceted exterior 129 that is adapted to mate with a similarly shaped socket of a closure driving or installation tool 145, described below. It is foreseen that different driving heads or other methods of driving the closure top 52 can be utilize with certain embodiments of the invention.

Additional tools are utilized to assemble the implant. In particular, FIG. 16 illustrates a rod pusher 136 on the left. The pusher 136 has an elongate shaft or rod 138 that is preferably received in and passes through the interior of the guides 9 and 10, such as the channel 90 of the guide tool 10. The pusher 136 also has a tip 139 for engaging and urging the rod 4 downward, where there is minor resistance, and a handle 141. It is foreseen that a pusher or gripper of the type that operates outside the guide tools 9 and 10 can be utilized, but is not preferred as such would normally require greater penetration of the skin 14 and more invasion of the patient.

Figure 18:
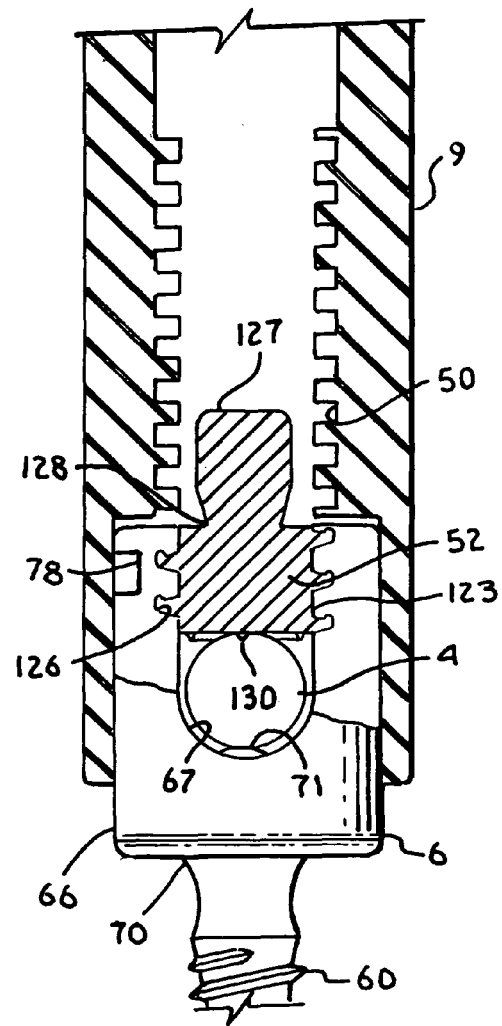
FIG. 18 is a view similar to FIG. 17 showing the rod and closure top installed in the bone screw before final torquing of the closure top.

Shown in FIG. 16 on the left and in FIG. 17 is the closure installation tool 145. The tool 145 has an elongate rod or shaft 147 adapted to be received in and pass axially through any of the channels of the guides 9 and 10 and a handle 149. The lower end of the rod 147 terminates in a socket 148 that is adapted to receive the closure break off head 127, as shown in FIG. 17.

Figure 20:
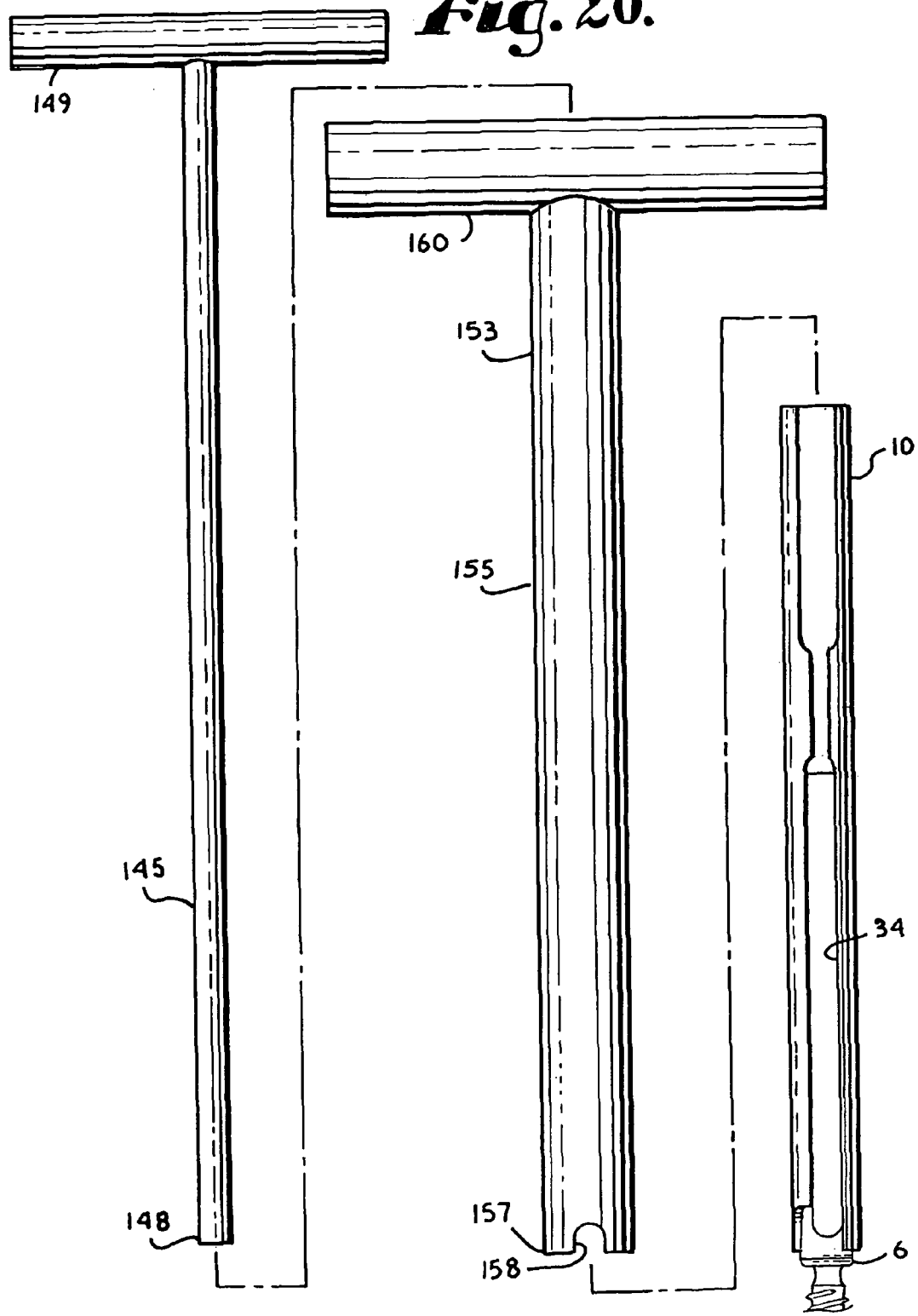
FIG. 20 is an exploded and front elevational view of a closure top installation tool, antitorque tool and one of the intermediate guide tools attached to a bone screw.

Another tool used in implanting a rod 4 is an antitorque tool 153 which is seen in FIGS. 20 to 22. The antitorque tool 153 is preferably used with the closure installation tool 145 to torque and set the closure top 52, so it is snug against the rod 4, and thereafter break away the break off head 127 in the manner shown in FIG. 22. The antitorque tool 153 includes a tubular hollow shaft 155 that is sized and shaped to be slidably received over the guide 9 and 10. The antitorque tool 153 has a lower end 157 that has a pair of diametrically spaced bridges 158. Each of the bridges 158 is sized and shaped to fit over the rod 4, as seen in FIG. 21. When in place, as seen in FIG. 21, the antitorque tool 153 allows a surgeon to counter torque applied by the installation tool 145, when applying torque to and breaking away the break off head 127. The antitorque tool 153 also has an upper handle 16 with an opening through which the installation tool 145 passes in the manner suggested by the dashed lines in FIG. 20.

In use, the previously described tools are utilized to attach one or more rods 4 to the human spinal column 17.

The procedure is begun by forming a relatively small incision, such as incision 165 in the skin 14 for each bone screw 6 to be used. The incisions 165 are stretched into a round shape with a circumference equal to or just slightly larger than the guide tools 9 and 10. The skin 14 is relatively flexible and allows the surgeon to move the incision 165 around relative to the spine 17 to manipulate the various tools and implants, as required. A drill (not shown) is utilized to form a guide bore (not shown) in a vertebra 18 under guidance of non invasive imaging techniques, which procedure is well known and established. A thin pin 166 is inserted in the guide bore. A bone screw 6 is selected in accordance with the size of the patient's vertebra 18 and the requirements of the spinal support needed. Bone screws 6 having a rotatable or poly axial head 66 are preferred for the procedure, as such allow relatively easy adjustment of the rod 4 in the tools 9 and 10 during placement and for movement of tools 9 and 10, as described below. The bone screw 6 is also cannulated so as to be receivable over and guided by the pin 166 toward the proper position in the associated vertebra 18.

Before placing the bone screw 6 in the vertebra 18, the bone screw 6 is preferably joined to an associated guide tool 9 or 10. This could be done after insertion of the bone screw 6, but it is preferred to assemble both before inserting the bone screw 6. With respect to the intermediate guide tool 10, the lower end of the guide tool 10 is splayed or expanded outwardly by forcing the bone screw head 66 between the legs 93 and 94, in the manner shown in FIG. 7 until the attachment structure 113 aligns with the receiver 78 and the former snaps into the later, as shown in FIG. 8. Axial upward movement of the guide tool 10 relative to the bone screw 6 then sets the attachment structure 113 in the recess 80 in the process that is illustrated between FIGS. 10 and 11. Alternatively, the tool 10 can be axially rotated ninety degrees relative to the bone screw 6 and the attachment structure 113 aligned with the recess 80 and then rotated back. The placement of the guide tools 9 on the associated bone screws 6 normally follows the later twist on procedure, as the structure of the guide tools 9 allow less flexing because of the longer back wall 21. With tool 9, the attachment structure 55 is placed in a respective receiver 55.

A series of bone screws 6 are installed in each vertebra 18 to be attached to the rod 4 by use of a screwdriver or installation tool 135, see FIG. 12, that has a head, designed to grip the particular bone screw 6 used and which is also cannulated to receive the pin 166. For each bone screw 6, an associated guide tool 9 or 10 extends through the skin 14, as seen in FIG. 13. An end guide tool 9 is located at each end of the series of bone screws 6 and an intermediate guide tool 10 is located on each intermediate bone screw 6. The end guide tools 9 are turned or rotated so the channels 34 therein face one another and the intermediate guide tools 10 are aligned so slots 105 align with the channels 34.

The rod 4 is then inserted diagonally through one of the end skin incisions 165 in the manner shown in FIG. 13 so that a first rod end 42 passes through the slots 105 in any intermediate guide tools 10 and into the channel 34 of the opposed end guide tool 9. Back muscle tissue separates easily here to allow the upper insertion of the rod 4 and can be further separated by finger separation or cutting through one of the incisions 165, if required.

After initial insertion, the second end 42 of the rod 4 is positioned in the channel 34 of the end guide tool 9 that is located next to the insertion point of the rod 4, as is seen in FIG. 14.

Figure 19:
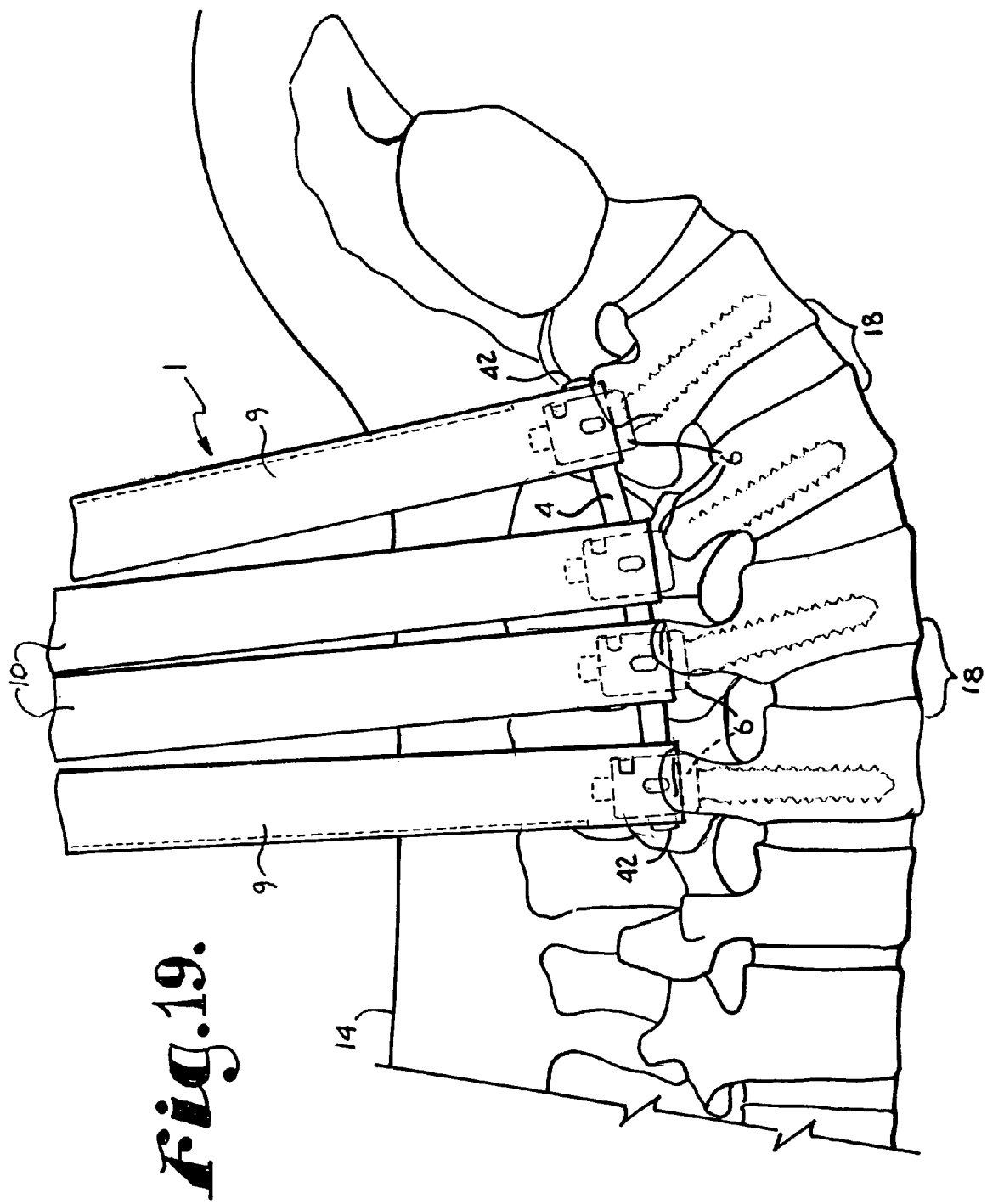
FIG. 19 is a partial and generally schematic side view of the spine showing the rod fully installed in the bone screws.

Once the rod 4 is positioned in the guide tools 9 and 10, a pusher tool 136 of the type shown in FIG. 16 is utilized to push the rod 4 in each guide tool 9 or 10 toward the bone screw 6 associated with the guide tool 9 or 10 until the rod 4 is in approximately the position seen in FIG. 15. During this time, the end guide tools 9 can be manipulated to help movement of the rod 4 therealong and can especially have the tops thereof splayed outwardly relative to each other, as seen in FIG. 15. Again, the flexibility of the skin 14 allows such manipulation. Once the rod 4 reaches the bottom 39 of the end guide tools 9, the rod ends 42 encounter the cut outs 45 on either side of the rod 4 and pass therethrough. The rod 4 is sized to extend a little beyond each end bone screw 6 to ensure full capture and reduce likelihood of dislodgement. Because the channels 34 are slightly inward of the full outer length of the rod 4, the channels 34 must be tilted outward somewhat as seen in FIG. 15 to allow the rod 4 to pass down the channels 34 or one end 42 must be driven downward before the other. When the rod 4 is at the bottom of the guide tools 9 and 10, such as seen in FIG. 19, the end guide tools 9 can be returned to a position that is appropriate for properly aligning the bone screw heads 6 relative to the rod 4 prior to tightening and torquing the closure tops 52. Because the rod 4 is normally bent and/or the vertebrae 18 do not align properly, the rod 4 must normally be biased into the bone screw heads 6. This is accomplished by using the closure installation tool 145 in the manner illustrated on the right hand side in FIG. 16 and in FIG. 17.

In particular, the tool 145 has a socket 148 that grips the break off head 127 of the closure top 52. The installation tool 145 with closure top 52 therein is placed in the elongate top to bottom channel associated with the guide tools 9 and 10 either by entry from the side such as into channel 25 through opening 26 in guide tool 9 or into channel 25 through the top end 38 of the guide tool 9. The closure top 52 is then driven under manual control of the surgeon by use of the installation tool 145 toward the rod 4. Near the bottom of the guide tools 9 and 10, such as near the bottom 39 of end guide tool 9, the closure top 52 engages the helical wound first guide and advancement structure 50 and the tool 145 and closure top 52 are rotated mate the closure top helical mating structure 125 with the first guide and advancement structure 50 so as to drive the closure top 52 downward against the rod 4 and to urge the rod 4 downward into the bone screw channel 67. At the bottom of the guide tool 9 or 10, the closure top mating structure 125 engages and begins to mate with the guide and advancement structure 76 on a respective bone screw 6 and continued rotation of the tool 145 drives the rod 4 downward and into engagement with the dome 71 of the bone screw shank 60, so as to snug against and frictionally lock the shank 60 in position relative to the bone screw head 66, see FIG. 18.

Once all of the closure tops 52 are in final seating position in respective bone screws 6 and the surgeon is satisfied with the position of all of the elements, such as is seen in FIG. 19, the antitorque tool 153 is mounted over each guide tool 9 or 10, as shown in FIG. 21 with the bridges 158 straddling the rod 4 to prevent rotation. The installation tool 145 is inserted in the associated guide tool 9 or 10 and engaged with the break off head 127. By cooperative use of the tools 145 and 153 a preselected torque is manually applied to the break off head 127 and it breaks from the closure top body 123 in the manner shown in FIG. 22 and is removed along with the antitorque tool 153.

Figure 23:
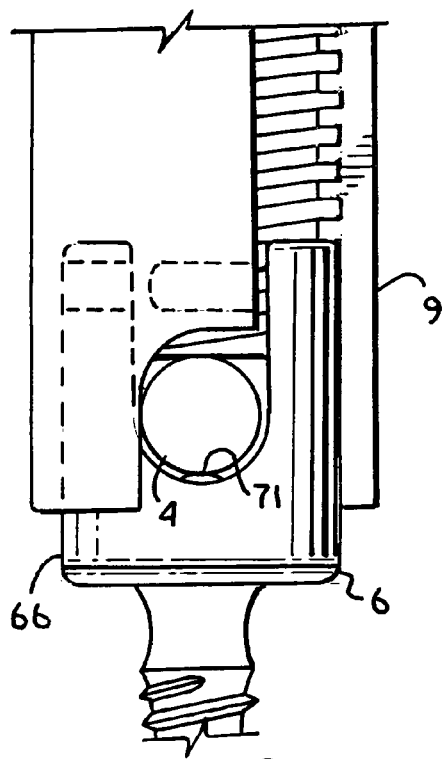
FIG. 23 is a fragmentary and enlarged front elevational view showing an early stage in the removal of the end guide tool from the bone screw wherein the tool has been rotated approximately ninety degrees relative to its axis to the shown removal configuration from the installation configuration, such as seen in FIG. 17, thereof.
Figure 24:
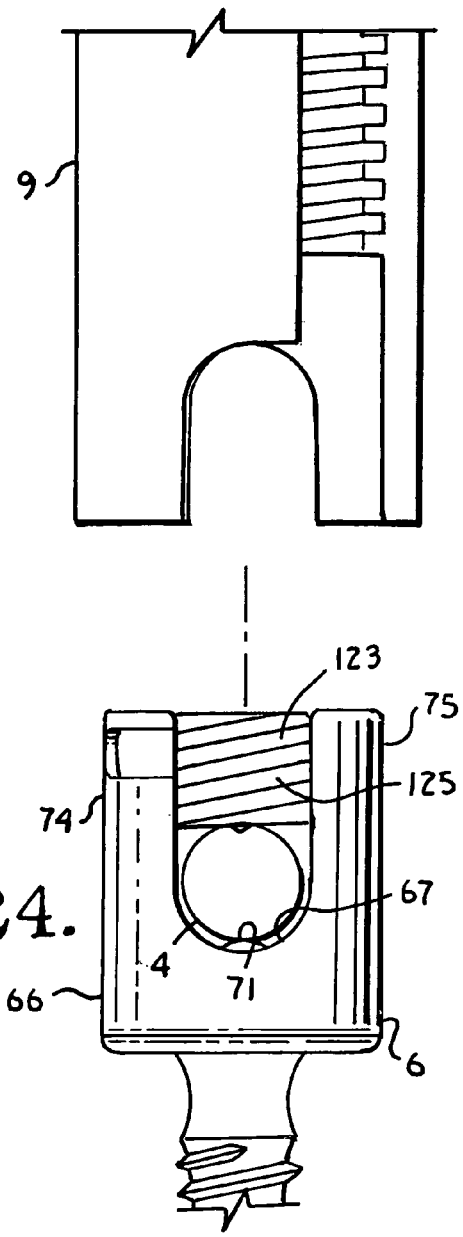
FIG. 24 is a fragmentary and enlarged front elevational view showing the end guide tool disengaged from the bone screw.

The guide tools 9 and 10 are then each rotated ninety degrees to align the attachment structure, such as structures 55 and 113 with the opening between bone screw arms 74 and 75, as shown in FIG. 23, so that the recess 49 straddles the rod 4 to allow the attachment structure 55 or 113 to disengage from the receiver 78. The guide tool 9 or 10 is then pulled axially upward away from the bone screw 6 and from the incision 165 in the skin 14, after which the incision 165 is closed.

It is to be understood that while certain forms of the present invention have been illustrated and described herein, it is not to be limited to the specific forms or arrangement of parts described and shown.

What is claimed and desired to be secured by Letters Patent is as follows:

1. A tool set for implanting a spinal rod in a patient; said tool set comprising:
    a) a pair of end guide tools;
    b) each of said end guide tools being adapted to removably attach at a lower end thereof to a respective spinal implant bone screw; and
    c) each of said end guide tools including:
        i) a longitudinally extending central axis;
        ii) a central bore coaxial with the central axis and extending from said lower end to an upper end of said end guide tool; and
        iii) a longitudinal guide channel extending upwardly from said lower end thereof; wherein
        vi) said guide channel extends radially outward from said bore; said guide channel being sized and shaped to receive a rod for operably guiding the rod toward a respective removably attached bone screw.

2. The tool set according to claim 1 wherein said tool set further includes:
    a) at least one intermediate guide tool, including:
    b) each of said intermediate guide tools including an attachment structure at a bottom end thereof, said attachment structure being adapted for removable attachment to a respective spinal implant bone screw;
    c) each of said intermediate guide tools including a central longitudinal axis;
    d) a longitudinal bore coaxial with said longitudinal axis and extending from said bottom end to said top end; and
    e) a longitudinal pass through slot extending radially outward from said central longitudinal bore and extending from said bottom end toward said top end of each intermediate guide tool and being adapted to receive therethrough and operably guide the rod toward a respective removably attached bone screw.

3. The tool set according to claim 1 wherein:
    a) said longitudinal guide channel is sized to slidingly receive both the rod end and a closure for the respective removably attached bone screw.

4. The tool set according to claim 3 wherein:
    a) each of said end guide tools has a cutout region between said longitudinal guide channel and said end guide tool lower end; said cutout being open in a rear thereof so as to define a lower pass through slot sized and shaped to be adapted to allow passage therethrough of the rod end after the rod has been guided to near the bone screw by said longitudinal guide channel.

5. The tool set according to claim 1 wherein:
    a) each of said end guide tools has a lower attachment structure adapted to removably attach to a respective bone screw; and
    b) each of said end guide tool attachment structures including a curved hook member that is sized and shaped to be adapted to be received in a receiver on a respective bone screw when said hook member is aligned with the receiver and rotated axially.

6. The tool set according to claim 2 wherein:
    a) said intermediate guide tool longitudinal pass through slot extending to an intermediate location along the longitudinal bore; and
    b) said intermediate guide tool further including an upper channel extending radially outward from said longitudinal bore and extending upwardly from said intermediate location to said top end; said upper channel being joined with said longitudinal pass through slot.

7. The tool set according to claim 1 wherein:
    a) each of said end guide tools includes a lower end recess along said longitudinal guide channel that is sized and shaped to abut against and bridge a portion of the rod during removal of said end guide tool from the respective removably attached bone screw, so that said end guide tool can be rotated relative to the respective removably attached bone screw from an attachment configuration to a removal configuration with said recess being received around the rod; said recess having a curvature that is sized and shaped to be substantially the same as the rod.

8. The tool set according to claim 1, wherein said central bore includes an internal helically wound guide and advancement structure located at said lower end, said guide and advancement structure being sized and shaped to cooperate with mating threads on a separate structure, so as to operably guide the rod end into a head of the respective removably attached bone screw.

9. The tool set according to claim 2, wherein said longitudinal bore includes an internal helically wound threadform located at said bottom end, said guide and advancement structure being sized and shaped to cooperate with mating threads on a separate structure, so as to operably guide the rod into a head of the respective removably attached bone screw.

10. In a guide tool for implanting a spinal rod in a bone screw, the improvement comprising:
    a) an outwardly open elongate lower channel sized and shaped to be operably located at least partially beneath a patient's skin during use and adapted to guide a rod to a bone screw removably connected to said guide tool; and
    b) an outwardly open upper channel that is sized and shaped to be side loaded so as to receive a closure top for the bone screw and being operably located above the patient's skin during use; said upper channel being connected with said lower channel so as to form a longitudinally extending pass-through passageway to allow said closure top into said lower channel from said upper channel.

11. The guide tool according to claim 10, wherein said lower channel includes an internal helically wound guide and advancement structure at lower end thereof, said guide and advancement structure being sized and shaped to cooperate with mating threads on a separate structure, so as to operably guide the rod end into a head of the respective removably attached bone screw.

12. A tool for implanting spinal implants in a patient; said tool comprising:
    a) a body adapted to removably attach at a lower end thereof to a first spinal implant; and
    b) said body including a radially outwardly opening longitudinal guide channel extending upward from a lower end of said body; said channel being sized and shaped to be adapted to receive a rod-like second spinal implant for operably guiding the second spinal implant toward the first spinal implant.

13. The tool according to claim 12, the body including:
   a) a lower portion that is sized and shaped to be located beneath a patient's skin during use and an upper portion located outside of the patient during use; and
   b) said lower portion having an attachment structure thereon adapted to removably attach said tool to the first spinal implant.

14. The tool according to claim 12, wherein said longitudinal guide channel includes an internal helically wound guide and advancement structure at lower end thereof, said guide and advancement structure being sized and shaped to cooperate with mating threads on a separate structure, so as to operably guide the rod end into a head of the respective removably attached bone screw.

15. A tool set for implanting a spinal rod in a patient; said tool set comprising:
   a) a pair of elongate guide tools;
   b) each of said guide tools being adapted to releasably attach at a lower end thereof to a respective spinal implant bone anchor; and
   c) each of said guide tools including a longitudinal guide channel extending upwardly from said lower end thereof; said tool channel opening radially outward and being sized, shaped and aligned to receive and operably guide a rod toward a respective releasably attached bone anchor.

16. The tool according to claim 15, wherein said longitudinal guide channel includes an internal helically wound guide and advancement structure at said lower end, said guide and advancement structure being sized and shaped to cooperate with mating threads on a separate structure, so as to operably guide the rod end into a head of the respective removably attached bone screw.

17. A tool set for implanting a rod in the spine of a patient comprising:
   a) an elongate guide tool adapted to be detachably joined to a bone screw receiver;
   b) the guide tool having a central top to bottom bore; and
   c) the bore including internal guide and advancement threads adapted for mating with mating threads on a reduction tool.

18. The tool set according to claim 17 including the reduction tool; the guide tool and reduction tool cooperating during use to urge a receiver and rod together so that the rod seats in the receiver.

19. The tool set according to claim 18 including a closure wherein the closure is positioned on a lower end of the reduction tool and is urged against a rod during reduction to urge the rod to seat in receiver after which the closure operable closes the receiver and secures the rod in the receiver.

20. A tool set for implanting a spinal rod in a patient comprising:
   a) a guide tool that is adapted to be detachably joinable at a lower end to a bone screw receiver;
   b) the guide tool having a central axis extending from a bottom to a top thereof;
   c) the guide tool having a bore extending along the central axis from the bottom to the top of the guide tool; and
   d) the guide tool having a radially outwardly opening channel extending upward from the lower end of the guide tool with the channel also opening into the bore.

21. The tool set according to claim 20 including guide tool threads adapted to mate and cooperate with mating threads on a reduction tool.

22. The tool set according to claim 21 including the reduction tool and wherein the guide tool threads are within the bore.

23. A tool set for implanting a rod in the spine of a patient comprising:
   a) an elongate guide tool adapted to be detachably joined to a bone screw receiver and having a rod receiving side channel;
   b) the guide tool having a central top to bottom bore, the bore communicating with the side channel; and
   c) the bore including internal guide and advancement structure adapted for mating with mating guide and advancement structure on a receiver closure top.

24. A tool set for implanting a rod in the spine of a patient comprising:
   a) an elongate guide tool adapted to be detachably joined to a bone screw receiver and having a rod receiving side channel;
   b) the guide tool having a central top to bottom bore, the bore communicating with the side channel; and
   c) the bore including internal guide and advancement structure adapted for mating with mating guide and advancement structure within the receiver when joined to the tool.

25. A tool set for implanting a rod in the spine of a patient comprising:
   a) an elongate guide tool adapted at a lower end thereof to be detachably joined to a bone screw receiver;
   b) the guide tool having a central top to bottom bore; and
   c) the bore including internal guide and advancement structure adapted at the lower end thereof for mating with mating guide and advancement structure within the bone screw receiver when joined to the tool.

* * * * *